United States Patent [19]

Ienaga et al.

[11] Patent Number: 5,110,797
[45] Date of Patent: May 5, 1992

[54] PEPTIDE COMPOUND AND A PHARMACEUTICALLY ACCEPTABLE SALT THEREOF

[75] Inventors: Kazuharu Ienaga; Kunihiko Higashiura, both of Katoh, Japan

[73] Assignee: Nippon Zoki Pharmeceutical Co., Ltd., Osaka, Japan

[21] Appl. No.: 188,567

[22] Filed: Apr. 29, 1988

[30] Foreign Application Priority Data

Oct. 14, 1985 [JP] Japan .................. 60-229648

[51] Int. Cl.$^5$ .................. A61K 31/415; C07C 9/24; C07D 233/61
[52] U.S. Cl. .................. 514/19; 514/400; 514/419; 514/423; 514/626; 548/344; 548/496; 548/537; 562/564; 562/565; 562/442; 562/445; 562/557; 562/559
[58] Field of Search .................. 514/19, 400, 419, 423, 514/626; 548/344; 562/442, 445, 564, 565, 557, 559

[56] References Cited

U.S. PATENT DOCUMENTS 5,021,430 6/1991 Ksander .................. 514/400

FOREIGN PATENT DOCUMENTS 0312502 4/1989 European Pat. Off.
159756 9/1984 Japan.

OTHER PUBLICATIONS

Sadano et al. "Janolusimide . . .", Tetrahedron Lett., vol. 27, No. 22, pp. 2505-2508, 1986.
The McGraw-Hill Dictionary of Scientific & Technical Terms, p. 330.
Chem Abstracts 101:121904b, L-Ornithyltairine, Toda et al from J. Agric Food Chem, 1984, 32(5), 992-6.

Primary Examiner—Mary C. Lee
Assistant Examiner—M. S. H. Gabilan
Attorney, Agent, or Firm—Armstrong, Nikaido, Marmelstein, Kubovcik & Murray

[57] ABSTRACT

Peptide compounds of formula (I):

$$A-X-NH-Y-\overset{O}{\underset{\|}{C}}-R \quad (I)$$

wherein A is hydrogen or an amino-protecting group; X is a member selected from the group consisting of Gly, Glu, Tyr, Asp, Phe, Ile, Ala, Pro, Leu, Hyp, Val, His, Arg, Ser, Thr, Pyr, Trp, 5-HTP, Cys, Met, $\tau$-Glu, $\beta$-Asp; Y is a $(CH_2)_{3-6}$ or $(CH_2)_{3-6}$ having an hydroxy group; R is an hydroxy group or an oxygen atom with a carboxy-protecting group; are useful as neurotropic agents.

10 Claims, No Drawings

PEPTIDE COMPOUND AND A PHARMACEUTICALLY ACCEPTABLE SALT THEREOF

DETAILED DESCRIPTION OF THE INVENTION

The present invention relates to a novel peptide compound and a pharmaceutically acceptable salt thereof.

Recently various peptides and their derivatives have been synthesized, and their actions on the organism have been examined. Upon strenuously having made the study, the present inventors have found novel peptide compounds which have neurotropic effect, and thus have accomplished the present invention.

An object of the present invention is to provide a novel peptide compound useful as medicine and/or synthetic intermediate. Another object of the invention is provide a method for manufacturing such a novel peptide compound.

The novel peptide compound according to the present invention has the following formula (I):

wherein A is hydrogen atom, an amino-protecting group, an acidic amino acid residue or an acidic amino acid residue having a protecting group; X is a member selected from the group consisting of Gly, Glu, Lys, Tyr, Asp, Phe, Ile, Ala, Pro, Leu, Hyp, Val, His, Arg, Ser, Thr, Pyr, Trp, 5-HTP, Cys, Met, τ-Glu, β-Asp and any of the preceding compounds combined with a protecting group; Y is a straight alkylene group of 2 to 6 carbon atoms or a straight alkylene group of 2 to 6 carbon atoms having a hydroxy group; R is a hydroxy group or an oxygen atom with a carboxy-protecting group.

The peptide compounds and amino acids in the present application are expressed by the abbreviations adopted by IUPAC and IUB or by the abbreviations commonly used in the art to which the present invention pertains.

For example, the following abbreviations are used.

| | | | |
|---|---|---|---|
| Gly: | Glycine | Ala: | Alanine |
| Val: | Valine | Leu: | Leucine |
| Ile: | Isoleucine | Phe: | Phenylalanine |
| Pro: | Proline | Ser: | Serine |
| Thr: | Threonine | Tyr: | Tyrosine |
| Lys: | Lysin | Hyp: | Hydroxyproline |
| His: | Histidine | Asp: | Aspartic acid |
| Arg: | Arginine | Glu: | Glutamic acid |
| Trp: | Tryptophan | 5-HTP: | 5-HydroxyTryptophan |
| Cys: | Cysteine | Met: | Methionine |
| Pyr: | Pyroglutamic acid | β-Ala: | β-Alanine |
| GABA: | γ-Aminobutyric acid | EACA: | ε-Aminocaproic acid |
| GABOB: | γ-Amino-β-hydroxybutylic acid | | |

The amino acid residue in the present invention may be any of the D-isomer, L-isomer and DL-isomer.

In the above formula (I), A is hydrogen atom, an amino-protecting group, an acidic amino acid residue or an acidic amino residue having a protecting group. As the amino-protecting group, any protecting group of an amino group employed in conventional peptide synthesis can be employed, i.e. a lower alkoxycarbonyl group such as t-butoxycarbonyl or t-pentoxycarbonyl group, an aralkyloxycarbonyl group such as benzyloxycarbonyl group, or an aralkyloxycarbonyl group having a substituent such as o-chlorobenzyloxycarbonyl, p-nitrobenzyloxycarbonyl or p-methoxybenzyloxycarbonyl group.

A acidic amino acid residue is α-Glu, γ-Glu, α-Asp or β-Asp. As a protecting group of a terminal amino group of the acidic amino acid residue, the above mentioned amino-protecting group can be employed. A protecting group of a free carboxy group of the acidic amino acid residue is any protecting group employed in conventional peptide synthesis, i.e. an aralkyloxy group such as benzyloxy group, or an aralkyloxy group having a substituent such as p-methoxybenzyloxy etc., or 4-pyridiloxy group.

X is a member selected from the group consisting of Gly, Glu, Lys, Tyr, Asp, Phe, Ile, Ala, Pro, Leu, Hyp, Val, His, Arg, Ser, Thr, Pyr, Trp, 5-HTP, Cys, Met, γ-Glu, β-Asp and any of the preceding compounds combined with a protecting group. As a protecting group of the amino acid, any protecting group employed in conventional peptide synthesis can be employed, i.e. the protecting group of an amino or carboxy group as mentioned above, or a hydroxy-protecting group such as a benzyl group.

Y is a straight alkylene group of 2 to 6 carbon atoms such as ethylene, propylene, butylene, pentylene or hexylene group, or a straight alkylene group of 2 to 6 carbon atoms having one or more hydroxy groups, preferably one hydroxy group. Namely the amino acid residue at C-terminal containing the Y group is preferably GABA, β-Ala, GABOB or EACA.

R represents a hydroxy group or an oxygen atom with a carboxy-protecting group as mentioned above.

Preferred peptide compounds of the present invention include:

Gly-GABA, Ala-GABA, Val-GABA, Leu-GABA, Ile-GABA, Phe-GABA, Pro-GABA, Ser-GABA, Thr-GABA, Tyr-GABA, Hyp-GABA, Lys-GABA, His-GABA, Arg-GABA, Asp-GABA, Glu-GABA, β-Asp-GABA, γ-Glu-GABA, D-Asp-GABA, D-β-Asp-GABA, Pyr-GABA, Trp-GABA, 5-HTP-GABA, Cys-GABA, Met-GABA, Gly-β-Ala, Ala-β-Ala, Val-β-Ala, Leu-β-Ala, Ile-β-Ala, Phe-β-Ala, Pro-β-Ala, Ser-β-Ala, Thr-β-Ala, Tyr-β-Ala, Hyp-β-Ala, Lys-β-Ala, His-β-Ala, Arg-β-Ala, Asp-β-Ala, Glu-β-Ala, β-Asp-β-Ala, γ-Glu-β-Ala, D-Asp-β-Ala, D-β-Asp-β-Ala, Pyr-β-Ala, Trp-β-Ala, 5-HTP-β-Ala, Cys-β-Ala, Met-β-Ala, Gly-GABOB, Ala-GABOB, Val-GABOB, Leu-GABOB, Ile-GABOB, Phe-GABOB, Pro-GABOB, Ser-GABOB, Thr-GABOB, Tyr-GABOB, Hyp-GABOB, Lys-GABOB, His-GABOB, Arg-GABOB, Asp-GABOB, Glu-GABOB, β-Asp-GABOB, γ-Glu-GABOB, D-Asp-GABOB, D-β-Asp-GABOB, Pyr-GABOB, Trp-GABOB, 5-HTP-GABOB, Cys-GABOB, Met-GABOB, Gly-EACA, Ala-EACA, Val-EACA, Leu-EACA, Ile-EACA, Phe-EACA, Pro-EACA, Ser-EACA, Thr-EACA, Tyr-EACA, Hyp-EACA, Lys-EACA, His-EACA, Arg-EACA, Asp-EACA, Glu-EACA, β-Asp-EACA, γ-Glu-EACA, D-Asp-EACA, D-β-Asp-EACA, Pyr-EACA, Trp-EACA, 5-HTP-EACA, Cys-EACA, Met-EACA, γ-Glu-Gly-GABA, γ-Glu-Ala-GABA, γ-Glu-Val-GABA, γ-Glu-Leu-GABA, γ-Glu-Ile-GABA, γ-Glu-Phe-GABA, γ-Glu-Pro-GABA, γ-Glu-Ser-GABA, γ-Glu-Thr-GABA, γ-Glu-Tyr-GABA, γ-Glu-Hyp-GABA, γ-Glu-Lys-GABA, γ-Glu-His-GABA, γ-Glu-

Arg-GABA, γ-Glu-Asp-GABA, γ-Glu-Glu-GABA, γ-Glu-β-Asp-GABA, γ-Glu-γ-Glu-GABA, γ-Glu-D-Asp-GABA, γ-Glu-D-β-Asp-GABA, γ-Glu-Trp-GABA, γ-Glu-5-HTP-GABA, γ-Glu-Cys-GABA, γ-Glu-Met-GABA, γ-Glu-Phe-β-Ala, γ-Glu-Phe-GABOB, γ-Glu-Phe-EACA, Glu-Phe-GABA, Glu-Phe-β-Ala, Glu-Phe-GABOB, Glu-Phe-EACA, Asp-Phe-GABA, Asp-Phe-β-Ala, Asp-Phe-GABOB, Asp-Phe-EACA, β-Asp-Phe-GABA, β-Asp-Phe-β-Ala, β-Asp-Phe-GABOB, β-Asp-Phe-EACA, D-Asp-Phe-GABA, D-Asp-Phe-β-Ala, D-Asp-Phe-GABOB, D-Asp-Phe-EACA, D-β-Asp-Phe-GABA, D-β-Asp-Phe-β-Ala, D-β-Asp-Phe-GABOB, D-β-Asp-Phe-EACA, γ-Glu-Pro-β-Ala, γ-Glu-Pro-GABOB, γ-Glu-Pro-EACA, Glu-Pro-GABA, Glu-Pro-β-Ala, Glu-Pro-GABOB, Glu-Pro-EACA, Asp-Pro-GABA, Asp-Pro-β-Ala, Asp-Pro-GABOB, Asp-Pro-EACA, β-Asp-Pro-GABA, β-Asp-Pro-β-Ala, β-Asp-Pro-GABOB, β-Asp-Pro-EACA, D-Asp-Pro-GABA, D-Asp-Pro-β-Ala, D-Asp-Pro-GABOB, D-Asp-Pro-EACA, D-β-Asp-Pro-GABA, D-β-Asp-Pro-β-Ala, D-β-Asp-Pro-GABOB, D-β-Asp-Pro-EACA.

The peptide compounds of the present invention also include pharmaceutically acceptable salts of the compounds of the above formula (I), for example, salts as acid adduct with inorganic acids such as hydrochloric acid, sulfuric acid, nitric acid, hydrobromic acid, phosphoric acid, perchloric acid, thiocyanic acid, boric acid etc. or with organic acid such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid etc., and salts with metals such as alkali metal, e.g. sodium, potassium, lithium etc., and aluminum etc.

The peptide compounds of the invention can be include their metal complexes, for example complexes with zinc, nickel, cobalt, copper, iron etc.

These salts and metal complexes can be produced from free peptide compounds in the usual way or can be interchanged with each other.

The peptide compounds according to the present invention can be produced by conventional processes in peptide chemistry, and either the solution method or solid phase synthesis can be employed.

The coupling method for forming a peptide bond can include the azide method, active ester method, mixed acid anhydride method, acid chloride method, method employing a coupling reagent etc., and they can be employed either alone or combination according to the necessity.

As amino acid or peptide used as the starting material or materials in the coupling reaction, there are employed those having an appropriate substituent constituting group conventionally employed in peptide chemistry. Further, any carboxy group or amino groups which do not participate in the reaction can be protected by a known method, or any carboxy group or amino group which participates in the reaction can be activated.

The abbreviations used for the substitutes, reagents etc. are as follows:

Z: Benzyloxycarbonyl
Boc: t-Butoxycarbonyl
Bzl: Benzyl

| | |
|---|---|
| OBzl: | Benzyloxy |
| HONSu: | N-hydroxysuccinimide |
| ONSu: | N-hydroxysuccinimide ester |
| HONB: | N-hydroxy-5-norbornene-2,3-dicarboxyimide |
| ONB: | N-hydroxy-5-norbornene-2,3-dicarboxyimide ester |
| DSC: | Disuccinimidylcarbonate |
| DCC: | Dicyclohexylcarbodiimide |
| DCUrea: | Dicyclohexyl urea |
| WSCD: | 1-ethyl-3-(3-dimethylaminopropyl)carbodiimide (Water-soluble carbodiimide) |
| DCHA: | Dicyclohexylamine |
| NMM: | N-Methylmorpholine |
| TEA: | Triethylamine |
| THF: | Tetrahydrofuran |
| DMF: | Dimethylformamide |
| ECF: | Ethyloxycarbonyl chloride |
| TosOH: | p-Toluenesulfonic acid |

The peptide compounds of the present invention can be prepared as follows.

I. Preparation of Dipeptide compound

Method I (1):

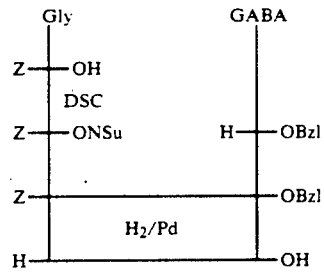

Method I (2):

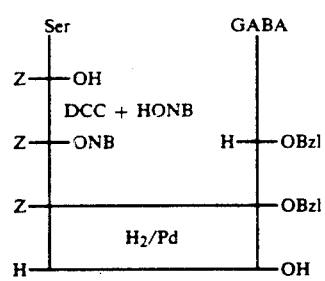

Method I (3):

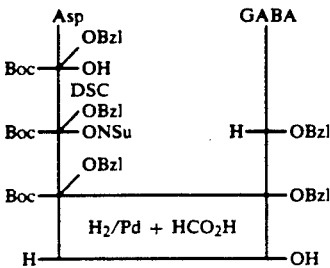

Method I (4):

-continued

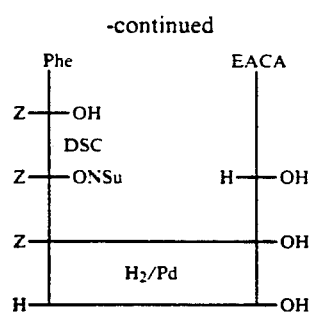

Method I (5):

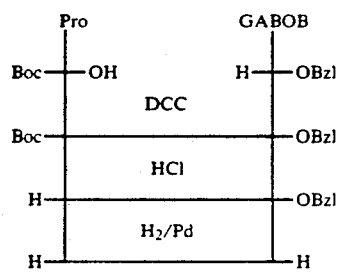

II. Preparation of Tripeptide compound

Method II (1):

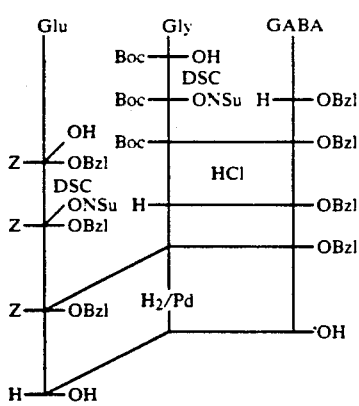

Method II (2):

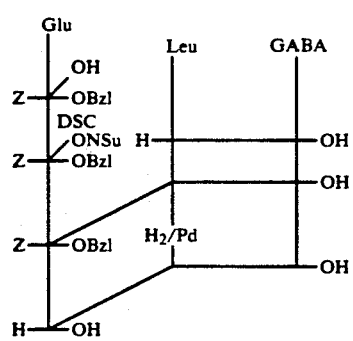

Method II (3):

-continued

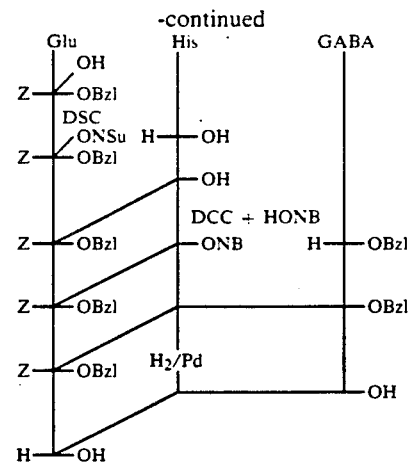

Method II (4):

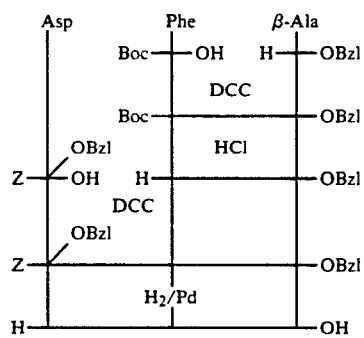

Method II (5):

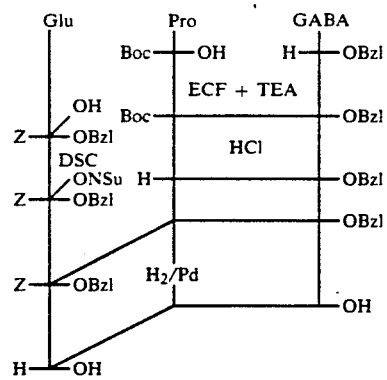

The above scheme illustrates a example of process for preparing a peptide compound of the present invention. Each of α-, β- or γ-amino acid can be similarly employed as the amino acid in the above schemes.

Method I(1)–(4) and Method II(1)–(3) show methods for preparing the peptide compounds of the invention according to the activated ester method using ONSu or ONB. The ONSu esterification can also be carried out by using both HOSu and DCC instead of DSC.

As the protecting group of an amino group at N-terminal and of the side chain, o-chlorobenzyloxycarbonyl, p-nitrobenzyloxycarbonyl or p-methoxybenzyloxycarbonyl group can be employed as well as benzyloxycarbonyl (Z), and t-pentoxycarbonyl or p-methoxybenzyloxycarbonyl group can be employed as well as t-butoxycarbonyl group (Boc).

As the protecting group of carboxy group at C-terminal and of the side chain, p-nitrobenzyloxy or 4- pyridiloxy group can be employed as well as benzyloxy group (OBzl). But it is not necessary to protect the carboxy group according to a kind of the reaction [Method I(4), Method II(2) and (3)]. The hydroxy group of the side-chain can be protected by benzyl group etc.

These substituents can be selectively or entirely removed by the conventional method such as catalytic reduction, acidolysis etc. either in the course of the synthetic process of the peptide compound of this invention or in its final stage. Further, if necessary, it is also possible to introduce a substituent which constitutes other peptide compound of the invention by conventional method.

Method II(1) shows that the amino acids which constitute the peptide compounds of the invention are condensed from C-terminal to N-terminal successively. On the other hand, Method II(3) is the peptide-elongating method from N-terminal to C-terminal. Therefore, the peptide compounds of the present invention can be prepared by either method elongating from N- or C-terminal.

Furthermore, instead of condensation of the constituent amino acid, the tripeptide of the present invention can be prepared by using the dipeptide of this invention such as Leu-GABA and the like as a starting material [Method II(2)].

DCC can be not used only as an esterifying agent forming active ester such as ONB etc. but also as a condensing agent directly forming peptide bond [Method I(5) and Method II(4)]. Water-soluble carbodiimide such as 1-ethyl-3-(3-dimethylaminopropyl)-carbodiimide hydrochloride can also be employed similarly to DCC as a condensing agent.

The peptide compounds of the present invention can be prepared by the mixed acid anhydride method [Method II(5)]. As an acidic component of the mixed acid anhydride, ethyloxycarbonyl chloride etc. can be employed, and triethylamine, N-methylmorphorinon etc. can be employed as a basic component.

The solvent available in preparations of the present invention is preferably inert to both starting materials and products, and preferably dissolves both, but suspending condition can also be employed. For example, tetrahydrofuran, ethyl acetate, dioxane, acetonitrile, chloroform, dichloromethane, dimethylformamide, dimethyl sulfoxide, hexamethyl phosphoroamide, benzene, ether, water, and a mixture thereof can be selected according to a kind of the reaction and employed.

The condensation reaction can be achieved by stirring for one hour to several days at −15 ° C. to room temperature, preferably for one hour to one day at 0 ° C. to room temperature.

As to the reaction to remove the protecting group, for example, reduction using Pd-C, it can be carried out for one hour to several days at −15 ° C. to room temperature, preferably for one hour to one day at 0 ° C. to room temperature. But when a strong acid such as hydrochloric acid is used, it is not preferred to allow the peptide product in the presence of the strong acid, therefore, preferably the reaction can be carried out for one to several hours.

EXAMPLES

The following examples, which are illustrative only and not intended to limit the scope of the invention, describe the preparation of the compounds of the present invention. The NMR was measured using t-butanol ($\delta = 1.23$ ppm) as the internal standard and expressed in the $\delta$ value, and the specific rotatory power was measured using sodium lump ($\lambda = 5893$ ° Å).

EXAMPLE 1

(i) To a suspension of 4.18 g of Z-Gly-OH and 5.12 g of DSC in 80 ml of acetonitrile, 1.58 g of pyridine in 20 ml of acetonitrile was added at room temperature and the mixture was stirred for 6 hrs to give Z-Gly-ONSu. Without purification, 7.31 g of TosOH.GABA-OBzl and 2.02 g of TEA were added to the solution at room temperature. After stirring for 20 hrs and evaporation in vacuo, the oily residue was dissolved in 100 ml of ethyl acetate. The solution was washed with water, 5% sodium hydrogencarbonate aqueous solution, brine, 10% citric acid aqueous solution, and brine. After dehydration over sodium sulfate anhydride, the organic layer was evaporated in vacuo to dryness. The crystalline residue was recrystallized from ethyl acetate/ether to give 6.43 g of Z-Gly-GABA-OBzl; yield 84%.

m.p.: 83.5°–85 ° C.

The following compounds were obtained in the same manner.

Z-Ala-GABA-OBzl
m.p.: 99.5°–100.5 ° C.
$[\alpha]^{22} = +6.43$ (c = 1.0, DMF)

Z-Val-GABA-OBzl
m.p.: 114.5°–116 ° C.
$[\alpha]^{25} = +10.1$ (c = 1.0, DMF)

Z-Leu-GABA-OBzl
m.p.: 73°–74 ° C.
$[\alpha]^{25} = -3.8$ (c = 1.0, DMF)

Z-Ile-GABA-OBzl
m.p.: 106.5°–109 ° C.
$[\alpha]^{25} = +6.7$ (c = 1.0, DMF)

(ii) 4.6 g of Z-Gly-GABA-OBzl was dissolved in a mixture of methanol (50 ml), acetic acid (30 ml) and water (5 ml), and hydrogenated in the presence of 2.0 g of 10% Pd-C at atmospheric pressure at room temperature. After stirring for 12 hrs and filtration, the reaction mixture was evaporated in vacuo to dryness. The residue was dissolved in a solution of ethanol (20 ml) and toluene (30 ml), and the remaining acetic acid was co-evaporated off with the solvent in vacuo. The procedure was repeated three times. The crystalline residue was recrystallized from water/ethanol to give 2.05 g of Gly-GABA (Compound 1).

m.p.: 212°–215 ° C. (Decomposition)
NMR(0.1NDCl/D$_2$O): $\delta = 1.77$(tt,2H,J$_1$=7.5 Hz,J$_2$=6.8 Hz), 2.25(t,2H,J=7.5 Hz), 3.25(t,2H,J=6.8 Hz), 3.77(s,1H)

The following compounds were obtained in the same manner.

Ala-GABA (Compound 2)
m.p.: 215°–218 ° C. (Decomposition)
$[\alpha]^{22} = +15.1$ (c = 1.0, H$_2$O)
NMR(0.1NDCl/D$_2$O): $\delta = 1.50$(d,3H,J=7.0 Hz), 1.78(tt,2H,J$_1$=7.0 Hz,J$_2$=7.0 Hz), 2.29(t,2H,J=7.0 Hz), 3.24(dt,1H,J$_1$=7.0 Hz,J$_2$=14.0 Hz), 3.27(dt,1H,J$_1$=7.0 Hz,J$_2$=14.0 Hz), 4.02(q,1H,J=7 Hz)

Val-GABA (Compound 3)
m.p.: 202°–203 ° C.
$[\alpha]^{22} = +40.7$ (c = 1.0, H$_2$O)
NMR(0.1NDCl/D$_2$O): $\delta = 1.01$(d,3H,J=7.0 Hz), 1.02(d,3H,J=7.0 Hz), 1.80(tt,2H,J$_2$=7.0 Hz,J$_2$=7.0 Hz), 2.12–2.24(m,1H), 2.31(t,2H,J=7.0 Hz), 3.24(dt,1H,J$_1$=7.0 Hz,J$_2$=14.0 Hz), 3.30(dt,1H,J$_1$=7.0 Hz,J$_2$=14.0 Hz), 3.72(d,1H,J=6.5 Hz)

Leu-GABA (Compound 4)
  m.p.: 179.5°–180.5 °C.
  $[\alpha]^{24} = +31.6$ (c=1.0, H$_2$O)
  NMR(0.1NDCl/D$_2$O): $\delta$=0.94(d,3H,J=6.0 Hz), 0.96(d,3H,J=6.0 Hz), 1.58–1.75(m,3H), 1.81(tt,2H,J$_1$=7.0 Hz,J$_2$=7.0 Hz), 2.36(t,2H,J=7.0 Hz), 3.22(dt,1H,J$_1$=7.0 Hz,J$_2$=14.0 Hz), 3.32(dt,1H,J$_1$=7.0 Hz,J$_2$=14.0 Hz), 3.94(t,1H,J=7.5 Hz)

Ile-GABA (Compound 5)
  m.p.: 152°–154 °C.
  $[\alpha]^{24} = +28.6$ (c=1.0, H$_2$O)
  NMR(0.1NDCl/D$_2$O): $\delta$=0.92(t,3H), 0.98(d,3H), 1.17–1.29(m,1H), 1.45–1.56(m,1H), 1.80(tt,2H,J$_1$=7.0 Hz,J$_2$=7.0 Hz), 1.89–2.00(m,1H), 2.34(t,2H,J=7.0 Hz), 3.23(dt,1H,J$_1$=7.0 Hz,J$_2$=14.0 Hz), 3.31(dt,1H,J$_1$=7.0 Hz,J$_2$=14.0 Hz), 3.79(d,2H,J=6.0 Hz)

EXAMPLE 2

(i) To a solution of 4.78 g of Z-Ser-OH and 4.34 g of HONB in 100 ml of THF, 4.54 g of DCC was added at 0 °C. and the mixture was stirred at 0 °C. for 1 h and at room temperature for 1 h to give Z-Ser-ONB. Precipitated DCUrea was filtered off and the filtrate was concentrated in vacuo. The oily product was dissolved in 100 ml of dioxane. 7.31 of TosOH.GABA-OBzl and 2.02 g of TEA were added to the solution at room temperature. After stirring for 20 hrs and evaporation in vacuo, the oily residue was dissolved in 100 ml of dichloromethane. The solution was washed with water, 5% sodium hydrogencarbonate aqueous solution, water, 10% citric acid aqueous solution, and water. After dehydration over sodium sulfate anhydride, the organic layer was evaporated in vacuo to dryness. The crystalline residue was recrystallized from ethyl acetate/ether to give 5.08 g of Z-Ser-GABA-OBzl; yield 61%.
  m.p.: 137°–138 °C.
  $[\alpha]^{25} = +17.5$ (c=1.0, DMF)

The following compounds were obtained in the same manner.

Z-Thr-GABA-OBzl
  m.p.: 94.5°–95.5 °C.
  $[\alpha]^{25} = +2.0$ (c=1.0, DMF)

Z-Tyr(Bzl)-GABA-OBzl
  m.p.: 138°–139 °C.
  $[\alpha]^{22} = -13.0$ (c=1.0, DMF)

Z-Hyp-GABA-OBzl
  m.p.: 73°–75 °C.
  $[\alpha]^{22} = -15.0$ (c=1.0, DMF)

Z-Phe-GABA-OBzl
  m.p.: 133°–134 °C.
  $[\alpha]^{22} = -8.9$ (c=1.0, DMF)

Z-Phe-GABOB-OBzl
  m.p.: 122°–123 °C.
  $[\alpha]^{25} = -9.1$ (c=1.0, DMF)

(ii) In the same manner as Example 1 (ii), 4.0 g of Z-Ser-GABA-OBzl was hydrogenated in the presence of Pd-C and removed the protecting group to give 1.50 g of Ser-GABA (Compound 6); yield 82%.
  m.p.: 188°–191 °C. (Decomposition)
  $[\alpha]^{24} = +12.5$ (c=1.0, H$_2$O)
  NMR(0.1NDCl/D$_2$O): $\delta$=1.79(tt,2H,J$_1$=7.5 Hz,J$_2$=7.5 Hz), 2.29(t,2H,J=7.5 Hz), 3.27(t,2H,J=7.5 Hz), 3.91(dd,1H,J$_1$=6.0 Hz,J$_2$=12.5 Hz), 3.97(dd,1H,J$_1$=4.0 Hz,J$_2$=12.5 Hz), 4.07(dd,1H,J$_1$=4.0 Hz,J$_2$=6.0 Hz)

The following compounds were obtained in the same manner.

Thr-GABA (Compound 7)
  m.p.: 136 °C. (Decomposition)
  $[\alpha]^{24} = +19.2$ (c=1.0, H$_2$O)
  NMR(0.1NDCl/D$_2$O): $\delta$=1.29(d,3H,J=6.5 Hz), 1.81(tt,2H,J$_1$=7.0 Hz,J$_2$=7.0 Hz), 2.37(t,2H,J=7.0 Hz), 3.28(t,2H,J=7.0 Hz), 3.79(d,1H,J=6.0 Hz), 4.12(dq,1H,J$_1$=6.0 Hz,J$_2$=6.5 Hz)

Tyr-GABA (Compound 8)
  NMR(0.1NDCl/D$_2$O): $\delta$=1.48–1.61(m,2H), 1.97–2.13(m,2H), 2.97(dt,1H,J$_1$=7.0 Hz,J$_2$=14.0 Hz), 3.00(dd,1H,J$_1$=9.0 Hz,J$_2$=14.0 Hz), 3.16(dd,1H,J$_1$=6.0 Hz,J$_2$=14.0 Hz), 3.29(dt,1H,J$_1$=7.0 Hz,J$_2$=14.0 Hz), 4.06(dd,1H,J$_1$=6.0 Hz,J$_2$=9.0 Hz), 6.86(d,2H,J=8.0 Hz), 7.13(d,2H,J=8.0 Hz)

Hyp-GABA (Compound 9)
  m.p.: 210°–211 °C.
  $[\alpha]^{24} = -35.8$ (c=1.0, H$_2$O) NMR(0.1NDCl/D$_2$O): $\delta$=1.80(tt,2H,J$_1$=7.0 Hz,J$_2$=7.0 Hz), 2.15(ddd,1H,J$_1$=3.5 Hz,J$_2$=10.0 Hz,J$_3$=14.0 Hz), 2.33(t,2H,J=7.0 Hz), 2.47(dddd,1H,J$_1$=2.0 Hz,J$_2$=2.0 Hz,J$_3$=8.0 Hz,J$_4$=14.0 Hz), 3.25(dt,1H,J$_1$=7.0 Hz,J$_2$=7.0 Hz), 3.31(dt,1H,J$_1$=7.0 Hz,J$_2$=14.0 Hz), 3.41(ddd,1H,J$_1$=2.0 Hz,J$_2$=3.5 Hz,J$_3$=12.5 Hz), 4.53(dd,1H,J$_1$=8.0 Hz,J$_2$=10.0 Hz), 4.68–4.72(m,1H)

Phe-GABA (Compound 10)
  m.p.: 173.5°–174.5 °C.
  $[\alpha]^{22} = +54.1$ (c=1.0, H$_2$O)
  NMR(0.1NDCl/D$_2$O): $\delta$=1.46–1.63(m,2H), 1.94–2.11(m,2H), 2.98(dt,1H,J$_1$=7.0 Hz,J$_2$=14.0 Hz), 3.09(dt,1H,J$_1$=9.0 Hz,J$_2$=14.0 Hz), 3.23(dd,1H,J$_1$=6.0 Hz,J$_2$=13.0 Hz), 3.25(dt,1H,J$_1$=7.0 Hz,J$_2$=14.0 Hz), 4.12(dd,1H,J$_1$=6.0 Hz,J$_2$=9.0 Hz), 7.24–7.42(m,5H)

Phe-GABOB (Compound 11)
  m.p.: 177 °C. (Decomposition)
  $[\alpha]^{25} = +60.3$ (c=1.1, H$_2$O)
  NMR90.1NDCl/D$_2$O): $\delta$=2.09–2.32(m,2H), 3.10–3.29(m,4H), 3.88–4.35(m,1H), 4.17–4.23(m,1H), 7.25–7.45(m,5H)

EXAMPLE 3

(i) To a suspension of 6.47 g of Boc-Asp(OBzl)-OH and 5.64 g of DSC in 80 ml of acetonitrile, 1.74 g of pyridine in 20 ml of acetonitrile was added at room temperature and the mixture was stirred for 12 hrs to give Boc-Asp(OBzl)-ONSu. Without purification, 7.31 g of TosOH.GABA-OBzl and 2.02 g of TEA was added to the mixture at room temperature. After stirring for 20 hrs and evaporation in vacuo, the oily residue was dissolved in 100 ml of ethyl acetate. The solution was washed with water, 5% sodium hydrogencarbonate aqueous solution, brine, 10% citric acid aqueous solution, and brine. After dehydration over sodium sulfate anhydride, the organic layer was evaporated in vacuo to dryness. The crystalline residue was recrystallized from ethyl acetate/ether/petroleum ether to give 7.94 g of Boc-Asp(OBzl)-GABA-OBzl; yield 80%.
  m.p.: 96°–98 °C.
  $[\alpha]^{24} = -11.3$ (c=1.1, DMF)

(ii) 4.98 g of Boc-Asp(OBzl)-GABA-OBzl was dissolved in 50 ml of 98% formic acid and hydrogenated in the presence of 1.0 g of 10% of Pd-C at atmospheric pressure at room temperature. After stirring for 3 days and filtration, the reaction mixture was evaporated in vacuo to dryness. Toluene was added to the residue and the remaining formic acid was coevaporated off with the solvent. The procedure was repeated three times. The crystalline residue was recrystallized from water- /ethanol to give 1.82 g of Asp-GABA (Compound 12); yield 83%.

m.p.: 216.5°–218 ° C. (Decomposition)
$[\alpha]^{25} = +12.6$ (c=0.5, 0.1NNaOH)
NMR(0.1NDCl/D$_2$O): $\delta = 1.81$(tt,2H,J$_1$=7.0 Hz,J$_2$=7.0 Hz), 2.40(t,2H,J=7.0 Hz), 2.95(dd,1H,J$_1$=7.0 Hz,J$_2$=18.0 Hz), 3.01(dd,1H,J$_1$=6.0 Hz,J$_2$=18.0 Hz), 3.23(dt,1H,J$_1$=7.0 Hz,J$_2$=13.5 Hz), 3.33(dt,1H,J$_1$=7.0 Hz,J$_2$=13.5 Hz), 4.27(dd,1H,J$_1$=6.0 Hz,J$_2$=7.0 Hz)

EXAMPLE 4

(i) To a solution of 0.52 g of GABA and 0.51 g of TEA in water/acetonitrile (10 ml/10 ml), 1.73 g of Z-Pro-ONSu and 30 ml of acetonitrile were added at room temperature. After stirring for 20 hrs, the solvent was distilled in vacuo and the residue was dissolved in a mixture of 20 ml of 1N HCl aqueous solution and 50 ml of ethyl acetate. The organic layer was separated and washed with brined and extracted with 5% sodium hydrocarbonate aqueous solution. The extract was washed with ethyl acetate and acidified with 6N aqueous HCl. The precipitated oil substance was extracted with ethyl acetate and the organic solution was washed with brine. After dehydration over sodium sulfate anhydride and evaporation in vacuo, the oily residue was triturated with petroleum ether and the crystalline product was recrystallized from ethyl acetate/ether to give 0.89 g of Z-Pro-GABA; yield 53%.

m.p.: 73°–75 ° C.
$[\alpha]^{22} = -29.5$ (c=1.0, DMF)

The following compounds were obtained in the same manner.

Z-Phe-β-Ala
m.p.: 136°–137 ° C.
$[\alpha]^{25} = -11.5$ (c=1.0, DMF)

Z-Phe-EACA
m.p.: 126°–128 ° C.
$[\alpha]^{25} = -10.2$ (c=1.0, DMF)

(ii) In the same manner as Example 1 (ii), 4.0 g of Z-Ser-GABA-OBzl was hydrogenated in the presence of Pd-C and removed the protecting group to give 1.50 g of Pro-GABA (Compound 13).

m.p.: 202°–205 ° C. (Decomposition)
$[\alpha]^{24} = -47.3$ (c=1.0, H$_2$O)
NMR(0.1NDCl/D$_2$O): $\delta = 1.79$(tt,2H,J$_1$=7.0 Hz,J$_2$=7.0 Hz), 1.97–2.11(m,3H), 2.29(t,2H,J=7.0 Hz), 2.36–2.49(m,1H), 3.24(dt,1H,J$_1$=7.0 Hz,J$_2$=14.0 Hz), 3.29(dt,1H,J$_1$=7.0 Hz,J$_2$=14.0 Hz), 3.34–3.77(m,2H), 4.32(dd,1H,J$_1$=7.0 Hz,J$_2$=8.0 Hz)

The following compounds were obtained in the same manner.

Phe-β-Ala (Compound 14)
m.p.: 218°–220 ° C. (Decomposition)
$[\alpha]^{25} = +63.4$ (c=1.0, H$_2$O)
NMR(0.1NDCl/D$_2$O):
$\delta$2.34(ddd,1H,J$_1$=5.0 Hz,J$_2$=8.0 Hz,J$_3$=17.0 Hz), 2.44(ddd,1H,J$_1$=5.0 Hz,J$_2$=6.0 Hz,J$_3$=17.0 Hz), 3.10(dd,1H,J$_1$=9.0 Hz,J$_2$=14.0 Hz), 3.21(dd,1H,J$_1$=6.0 Hz,J$_2$=14.0 Hz), 3.25(ddd,1H,J$_1$=5.0 Hz,J$_2$=8.0 Hz,J$_3$=14.0 Hz), 3.45(ddd,1H,J$_1$=5.0 Hz,J$_2$=6.0 Hz,J$_3$=14.0 Hz), 4.15(dd,1H,J$_1$=6.0 Hz,J$_2$=9.0 Hz), 7.20–7.43(m,5H)

Phe-EACA (Compound 15)
m.p.: 130 ° C. (Decomposition)
$[\alpha]^{25} = +42.9$ (c=1.1, H$_2$O)
NMR(0.1NDCl/D$_2$O): $\delta = 0.97$–1.07(m,2H), 1.22–1.34(m,2H), 1.48(tt,2H,J$_1$=7.0 Hz,J$_2$=7.0 Hz), 2.30(t,2H,J=7.0 Hz), 2.91–3.00(m,1H), 3.15–3.23(m,1H), 3.08(dd,1H,J$_1$=9.0 Hz,J$_2$=13.0 Hz), 3.22(dd,1H,J$_1$=6.0 Hz,J$_2$=13.0 Hz), 4.12(dd,1H,J$_1$=6.0 Hz,J$_2$=9.0 Hz), 7.20–7.45(m,5H)

EXAMPLE 5

(i) 2.02 g of TEA was added to a solution of 4.74 g of Boc-Pro-OH and 7.63 g of TosOH.GABOB-OBzl in 80 ml of dichloromethane. 4.54 g of DCC was added to the solution at 0 ° C., and the solution was stirred for 3 hrs at 0 ° C. and overnight at room temperature. Precipitated DCUrea was filtered off and the filtrate was evaporated in vacuo. The residue was dissolved in ethyl acetate and washed with 10% citric acid aqueous solution, water, 4% sodium hydrogencarbonate aqueous solution, and brine. After dehydration over sodium sulfate, the organic layer was evaporated in vacuo to dryness to give 7.93 g of Boc-Pro-GABOB-OBzl; yield 98%.

m.p.: oily substance
$[\alpha]^{26} = -45.7$ (c=1.1, CHCl$_3$)

The following compounds were obtained in the same manner.

Boc-Pro-β-Ala-OBzl
m.p.: oily substance
$[\alpha]^{26} = -53.9$ (c=1.2, CHCl$_3$)

Boc-Pro-EACA-OBzl
m.p.: oily substance
$[\alpha]^{22} = -42.9$ (c=1.1, CHCl$_3$)

Boc-Phe-β-Ala-OBzl
m.p.: 95.5°–96.5 ° C.
$[\alpha]^{22} = -0.20$ (c=1.0, CHCl$_3$)

Boc-Phe-GABOB-OBzl
m.p.: 103°–104 ° C.
$[\alpha]^{22} = +5.11$ (c=1.0, CHCl$_3$)

Boc-Phe-EACA-OBzl
m.p.: 102°–103 ° C.
$[\alpha]^{22} = +4.25$ (c=1.0, CHCl$_3$)

(ii) To a solution of 2.50 g of Boc-Pro-GABOB-OBzl in 20 ml of dioxane, 20 ml of 6N HCl/dioxane was added at room temperature. After stirring for 4 hrs, the solvent was distilled in vacuo and the residue was dissolved in a mixture of methanol (40 ml), acetic acid (10 ml) and water (5 ml). 0.25 g of 10% Pd-C was added to the solution. After stirring overnight at atmospheric pressure at room temperature, the catalyst was filtered off and the filtrate was concentrated in vacuo. Water was added to the residue and insoluble matter was filtered off. After concentration of the filtrate, the oily residue was triturated with water/ethanol to give 1.08 g of Pro-GABOB (Compound 16); yield 81%.

m.p.: 210°–212 ° C.
$[\alpha]^{26} = -40.5$ (c=1.3, 0.1NHCl)
NMR(0.1NDCl/D$_2$O): $\delta = 2.01$–2.11(m,3H), 2.41–2.54(m,2H), 2.58–2.65(m,1H), 3.30–3.48(m,3H), 4.13–4.22(m,1H), 4.37(dd,1H,J$_1$=7.0 Hz,J$_2$=8.0 Hz)

The following compounds were obtained in the same manner.

Pro-β-Ala (Compound 17)
m.p.: 218°–219 ° C. (Decomposition)
$[\alpha]^{26} = -50.8$ (c=1.0, H$_2$O)
NMR(0.1NDCl/D$_2$O): $\delta = 2.10$–2.18(m,3H), 2.38–2.47(m,1H), 2.64(t,2H,J=6.5 Hz), 3.35–3.46(m,2H), 3.49(dd,1H,J$_1$=6.5 Hz,J$_2$=13.0 Hz), 3.57(dd,1H,J$_1$=6.5 Hz,J$_2$=13.0 Hz), 4.35(dd,1H,J$_1$=7.0 Hz,J$_2$=8.0 Hz)

Pro-EACA (Compound 18)
m.p.: 182°–183 ° C.

[α]$^{25}$ = −47.6 (c = 1.0, H$_2$O)

NMR(0.1NDCl/D$_2$O): δ = 1.30–1.38(m,2H), 1.49–1.60(m,4H), 1.96–2.11(m,3H), 2.38(t,2H,J = 8.0 Hz), 2.39–2.49(m,1H), 3.19(dt,1H,J$_1$ = 7.0 Hz,J$_2$ = 14.0 Hz), 3.29(dt,1H,J$_1$ = 7.0 Hz,J$_2$ = 14.0 Hz), 3.35–3.48(m,2H), 4.33(t,1H,J = 7.5 Hz)

Phe-GABA (Compound 11)
Phe-β-Ala (Compound 14)
Phe-EACA (Compound 15)

EXAMPLE 6

(i) To a suspension of 3.50 g of Boc-Gly-OH and 5.12 g of DSC in 80 ml of acetonitrile, 1.58 g of pyridine in 20 ml of acetonitrile was added at room temperature and the mixture was stirred for 4 hrs to give Boc-Gly-ONSu. Without purification, 7.31 g of TosOH.GABA-OBzl and 2.02 g of TEA were added to the mixture at room temperature. After stirring for 20 hrs and evaporation in vacuo, the oily residue was washed with water, 5% sodium hydrogencarbonate aqueous solution, brine, 10% citric acid aqueous solution, and brine. After dehydration over sodium sulfate anhydride, the organic layer was evaporated in vacuo. The oily residue was crystallized from petroleum ether and recrystallized from ethyl acetate/ether/petroleum ether to give 5.54 g of Boc-Gly-GABA-OBzl; yield 79%.

m.p.: 94.0°–94.5 ° C.

(ii) 5.26 g of Boc-Gly-GABA-OBzl was treated with 75 ml of 4N HCl/dioxane at room temperature for 1.5 hrs. The solvent was distilled in vacuo and the oily residue was triturated with ether. The crystalline residue was collected by filtration and washed with ether. The product was dried over NaOH pellet in vacuo to give 4.21 g of HCl.Gly-GABA-OBzl. The resulting product was used without further purification.

(iii) 4.68 g of Z-Glu(ONSu)-OBzl was added to a solution of 3.15 g of HCl.Gly-GABA-OBzl and 1.11 g of TEA in 100 ml of acetonitrile at room temperature. After stirring for 20 hrs and evaporation in vacuo, the residue was dissolved in ethyl acetate. The solution was washed with water, 5% sodium hydrogencarbonate aqueous solution, brine, 10% citric acid aqueous solution, and brine. The solution was dried over sodium sulfate anhydride and evaporated in vacuo to dryness. The crystalline residue was recrystallized from ethyl acetate/ether to give 5.62 g of Z-Glu(Gly-GABA-OBzl)-OBzl.

m.p.: 107.5°–109.5 ° C.
[α]$^{24}$ = −7.5 (c = 1.0, DMF)

The following compounds were obtained in the same manner.

Z-Glu(Ala-GABA-OBzl)-OBzl
  m.p.: 165.5°–166.5 ° C.
  [α]$^{24}$ = −8.8 (c = 1.0, DMF)
Z-Glu(Ile-GABA-OBzl)-OBzl
  m.p.: 166°–170 ° C.
  [α]$^{24}$ = −5.3 (c = 1.1, DMF)
Z-Glu(Phe-GABA-OBzl)-OBzl
  m.p.: 154°–156 ° C.
  [α]$^{24}$ = −9.8 (c = 1.0, DMF)
Z-Glu(Pro-GABA-OBzl)-OBzl
  m.p.: 99°–100.5 ° C.
  [α]$^{24}$ = −36.0 (c = 1.0, DMF)
Z-Glu(Ser(OBzl)-GABA-OBzl)-OBzl
  m.p.: 120°–123 ° C.
  [α]$^{≃}$ = −2.3 (c = 1.1, DMF)
Z-Glu(Tyr(OBzl)-GABA-OBzl)-OBzl
  m.p.: 169°–170.5 ° C.
  [α]$^{24}$ = −11.0 (c = 1.0, DMF)
Z-Glu(Asp(OBzl)-GABA-OBzl)-OBzl
  m.p.: 129°–131 ° C.
  [α]$^{24}$ = −17.3 (c = 1.0, DMF)
Z-Glu(Glu(OBzl)-GABA-OBzl)-OBzl
  m.p.: 144°–145.5 ° C.
  [α]$^{24}$ = −7.5 (c = 1.0, DMF)
Z-Glu(Lys(Z)-GABA-OBzl)-OBzl
  m.p.: 140° C. (Decomposition)
  [α]$^{24}$ = −8.7 (c = 1.1, DMF)

(iv) 4.34 g of Z-Glu(Gly-GABA-OBzl)-OBzl was dissolved in a solution of methanol (40 ml), acetic acid (40 ml) and water (5 ml), and hydrogenated in the presence of 10% Pd-C (1.0 g) at atmospheric pressure at room temperature. After stirring for 2 days and filtration, the filtrate was evaporated in vacuo. 50 ml of toluene was added to the residue and the remaining acetic acid was coevaporated off with the solvent in vacuo. The procedure was repeated three times. The white precipitate was collected by filtration and recrystallized from water/ethanol to give 1.89 g of γ-Glu-Gly-GABA (Compound 19).

m.p.: 225°–226 ° C.
[α]$^{25}$ = +7.6 (c = 0.5, 0.1NNaOH)
NMR(0.1NDCl/D$_2$O): δ = 1.79(tt,2H,J$_1$ = 7.0 Hz,J$_2$ = 7.0 Hz), 2.16–2.31(m,2H), 2.39(t,2H,J = 7.0 Hz), 2.55(dt,1H,J$_1$ = 7.0 Hz,J$_2$ = 16.0 Hz), 2.60(dt,1H,J$_1$ = 7.0 Hz,J$_2$ = 16.0 Hz), 3.24(t,2H,J = 7.0 Hz), 3.86(s,2H), 4.09(t,1H,J = 6.5 Hz)

The following compounds were obtained in the same manner.

γ-Glu-Ala-GABA (Compound 20)
  m.p.: 187°–188 ° C.
  [α]$^{22}$ = −26.5 (c = 1.0, H$_2$O)
  NMR(0.1NDCl/D$_2$O): δ = 1.34(d,3H,J = 7.0 Hz), 1.77(tt,2H,J$_1$ = 7.0 Hz,J$_2$ = 7.0 Hz), 2.10–2.25(m,2H), 2.37(t,2H,J = 7.0 Hz), 2.49(dt,1H,J$_1$ = 7.0 Hz,J$_2$ = 15.0 Hz), 2.54(dt,1H,J$_1$ = 7.0 Hz,J$_2$ = 15.0 Hz), 3.20(dt,1H,J$_1$ = 7.0 Hz,J$_2$ = 14.0 Hz), 3.24(dt,1H,J$_1$ = 7.0 Hz,J$_2$ = 14.0 Hz), 4.00(t,1H,J = 7.0 Hz), 4.18(q,1H,J = 7.0 Hz)

γ-Glu-Ile-GABA (Compound 21)
  m.p.: 187°–190 ° C. (Decomposition)
  [α]$^{24}$ = −21.7 (c = 1.0, H$_2$O)
  NMR(0.1NDCl/D$_2$O): δ = 0.86(t,3H,J = 7.5 Hz), 0.90(d,3H,J = 7.0 Hz), 1.13–1.22(m,1H), 1.41–1.52(m,1H), 1.75–1.86(m,3H), 2.12–2.26(m,2H), 2.39(t,2H,J = 7.0 Hz), 2.52(dt,1H,J$_1$ = 8.0 Hz,J$_2$ = 16.0 Hz), 2.58(dt,1H,J$_1$ = 8.0 Hz,J$_2$ = 16.0 Hz), 3.22(dt,1H,J$_1$ = 7.0 Hz,J$_2$ = 14.0 Hz), 3.26(dt,1H,J$_1$ = 7.0 Hz,J$_2$ = 14.0 Hz), 4.02(t,1H,J = 6.5 Hz), 4.05(d,1H,J = 8.0 Hz)

γ-Glu-Phe-GABA.H$_2$O (Compound 22)
  m.p.: 174°–175 ° C. (Decomposition)
  [α]$^{24}$ = +4.1 (c = 1.0, H$_2$O)
  NMR(0.1NDCl/D$_2$O): δ = 1.50–1.62(m,2H), 2.00–2.18(m,4H), 2.48(t,2H,J = 7.5 Hz), 2.97–3.05(m,1H), 3.02(d,2H,J = 8.0 Hz), 3.20(dt,1H,J$_1$ = 7.0 Hz,J$_2$ = 14.0 Hz), 3.98(t,1H,J = 6.5 Hz), 4.47(t,1H,J = 8.0 Hz), 7.24–7.38(m,5H)

γ-Glu-Pro-GABA (Compound 23)
  m.p.: 55 ° C. (Decomposition)
  [α]$^{25}$ = −60.2 (c = 1.0, H$_2$O)
  NMR(0.1NDCl/D$_2$O): δ = 1.79(tt,2H,J$_1$ = 7.0 Hz,J$_2$ = 7.0 Hz), 1.89–2.03(m,3H), 2.13–2.29(m,3H), 2.39(t,H,J = 7.0 Hz), 2.65(t,2H,J = 7.0 Hz), 3.17–3.29(m,2H), 3.55–3.69(m,2H), 3.91(t,1H,J = 7.0 Hz), 4.33(dd,1H,J$_1$ = 7.0 Hz,J$_2$ = 8.0 Hz)

γ-Glu-Ser-GABA (Compound 24)
  m.p.: 175°-177 °C. (Decomposition)
  $[\alpha]^{22} = -15.6$ (c=1.0,H$_2$O)
  NMR(0.1NDCl/D$_2$O): $\delta = 1.79$(tt,2H,J$_1$=7.0 Hz,J$_2$=7.0 Hz), 2.20(dddd,1H,J$_1$=7.0 Hz,J$_2$=7.0 Hz,J$_3$=7.0 Hz,J$_4$=14.0 Hz), 2.26(dddd,1H,J$_1$=7.0 Hz,J$_2$=7.0 Hz,J$_3$=7.0 Hz,J$_4$=14.0 Hz), 2.39(t,2H,J=7.0 Hz), 2.57(ddd,1H,J$_1$=7.0 Hz,J$_2$=7.0 Hz,J$_3$=15.0 Hz), 2.62(ddd,1H,J$_1$=7.0 Hz,J$_2$=7.0 Hz,J$_3$=15.0 Hz), 3.23(ddd,1H,J$_1$=7.0 Hz,J$_2$=7.0 Hz,J$_3$=13.0 Hz), 3.28(ddd,1H,J$_1$=7.0 Hz,J$_2$=7.0 Hz,J$_3$=13.0 Hz), 3.82(d,1H,J=5.5 Hz), 4.08(t,p1H,J=7.0 Hz), 4.35(t,1H,J=5.5 Hz)

γ-Glu-Tyr-GABA (Compound 25)
  m.p.: 185°-186 °C.
  $[\alpha]^{22} = +6.3$ (c=1.0, AcOH)
  NMR(0.1NDCl/D$_2$O): $\delta = 1.50$-1.61(m,2H), 2.01(2.26(m,4H), 2.49(t,1H,J=8.0 Hz), 2.50(t,1H,J=8.0 Hz), 2.91(dd,1H,J$_1$=8.0 Hz,J$_2$=13.0 Hz), 2.96(dd,1H,J$_1$=8.0 Hz,J$_2$=13.0 Hz), 2.95-3.03(m,1H), 3.21(dt,1H,J$_1$=6.5 Hz,J$_2$=14.0 Hz), 4.01(t,1H,J=6.5 Hz), 4.40(t,1H,J=8.0 Hz), 6.82(d,2H,J=8.0 Hz), 7.12(d,2H,J=8.0 Hz)

γ-Glu-Asp-GABA (Compound 26)
  m.p.: 217°-218 °C. (Decomposition)
  $[\alpha]^{22} = +1.0$ (c=0.5, 0.1NNaOH)
  NMR(0.1NDCl/D$_2$O): $\delta = 1.78$(tt,2H,J$_1$=7.0 Hz,J$_2$=7.0 Hz), 2.15-2.29(m,2H), 2.38(t,2H,J=7.0 Hz), 2.54(dt,1H,J$_1$=7.5 Hz,J$_2$=15.0 Hz), 2.58(dt,1H,J$_1$=7.5 Hz,J$_2$=15.0 Hz), 2.81(dd,1H,J$_1$=8.0 Hz,J$_2$=16.5 Hz), 2.89(dd,1H,J$_1$=6.0 Hz,J$_2$=16.5 Hz), 3.25(t,2H,J=7.0 Hz), 4.09(t,1H,J=7.0 Hz), 4.64(dd,1H,J$_1$=6.0 Hz,J$_2$=8.0 Hz)

γ-Glu-Glu-GABA (Compound 27)
  m.p.: 179°-183 °C. (Decomposition)
  $[\alpha]^{22} = -11.2$ (c=1.0, H$_2$O)
  NMR(0.1NDCl/D$_2$O): $\delta = 1.79$(tt,2H,J$_1$=7.0 Hz,J$_2$=7.0 Hz), 1.96(ddt,1H,J$_1$=7.0 Hz,J$_2$=9.0 Hz,J$_3$=15.0 Hz), 2.09(ddt,1H,J$_1$=6.0 Hz,J$_2$=7.0 Hz,J$_3$=15.0 Hz), 2.14-2.25(m,2H), 2.39(t,2H,J=7.0 Hz), 2.47(t,2H,J=7.0 Hz), 2.48-2.60(m,2H), 3.22(dt,1H,J$_1$=7.0 Hz,J$_2$=14.0 Hz), 3.25(dt,1H,J$_1$=7.0 Hz,J$_2$=14.0 Hz), 3.97(t,1H,J=6.5 Hz), 4.26(dd,1H,J$_1$=6.0 Hz,J$_2$=9.0 Hz)

γ-Glu-Lys-GABA (Compound 28)
  m.p.: 277°-278 °C. (Decomposition)
  $[\alpha]^{22} = -10.1$ (c=1.0, AcOH)
  $\delta = 1.33$-1.50(m,2H), 1.63-1.79(m,4H), 1.79(tt,2H,J$_1$=7.0 Hz,J$_2$=7.0 Hz), 2.18(dddd,1H,J$_1$=7.0 Hz,J$_2$=7.0 Hz,J$_3$=7.0 Hz,J$_4$=15.0 Hz), 2.22(dddd,1H,J$_1$=7.0 Hz,J$_2$=7.0 Hz,J$_3$=7.0 Hz,J$_4$=15.0 Hz), 2.38(t,2H,J=7.0 Hz), 2.53(ddd,1H,J$_1$=7.0 Hz,J$_2$=7.0 Hz,J$_3$=15.0 Hz), 2.58(ddd,1H,J$_1$=7.0 Hz,J$_2$=7.0 Hz,J$_3$=15.0 Hz), 2.98(br.t,2H,J=7.5 Hz), 3.22(dt,1H,J$_1$=7.0 Hz,J$_2$=13.0 Hz), 3.26(dt,1H,J$_1$=7.0 Hz,J$_2$=13.0 Hz), 4.04(t,1H,J=7.0 Hz), 4.18(dd,1H,J$_1$=6.0 Hz,J$_2$=8.0 Hz)

EXAMPLE 7

(i) 1.62 g of Leu-GABA and 0.76 g of TEA were dissolved in a mixture of 30 ml of acetonitrile and 15 ml of water. 3.28 g of Z-Glu(ONSu)-OBzl and 20 ml of acetonitrile were added to the solution at room temperature with stirring. After stirring for 20 hrs and evaporation in vacuo, the residue was dissolved in a mixture of 50 ml of 1N HCl aqueous solution and 100 ml of chloroform. The organic layer was separated and washed with water and dehydrated over sodium sulfate anhydride. The solvent was distilled in vacuo and crystalline residue was recrystallized from chloroform/n-hexane to give 3.88 g of Z-Glu(Leu-GABA-OH)-OBzl; yield 97%.
  m.p.: 127.5°-129 °C.
  $[\alpha]^{24} = -14.9$ (c=1.0, DMF)
The following compounds were obtained in the same manner.
Z-Glu(Val-GABA-OH)-OBzl
  m.p.: 197°-198 °C.
  $[\alpha]^{24} = -5.2$ (c=1.0, DMF)
Z-Glu(Hyp-GABA-OH)-OBzl
  m.p.: 92°-94 °C.
  $[\alpha]^{24} = -28.9$ (c=1.0, DMF)

(ii) In the same manner as Example 6 (iv), 4.34 g of Z-Glu(Leu-GABA-OH)-OBzl was hydrogenated in the presence of Pd-C and removed the protecting group to give 1.25 g of γ-Glu-Leu-GABA (Compound 29); yield 60%.
  m.p.: 180°-181 °C.
  $[\alpha]^{24} = -22.3$ (c=1.0, H$_2$O)
  NMR(0.1NDCl/D$_2$O): $\delta = 0.87$(d,3H,J=6.0 Hz), 0.92(d,3H,J=6.0 Hz), 1.50-1.67(m,3H), 1.78(tt,2H,J$_1$=7.0 Hz,J$_2$=7.0 Hz), 2.13-2.27(m,2H), 2.38(t,2H,J=7.0 Hz), 2.52(dt,1H,J$_1$=7.5 Hz,J$_2$=15.0 Hz), 2.58(dt,1H,J$_1$=7.5 Hz,J$_2$=15.0 Hz), 3.20(dt,1H,J$_1$=7.0 Hz,J$_2$=14.0 Hz), 3.26(dt,1H,J$_1$=7.0 Hz,J$_2$=14.0 Hz), 4.06(t,1H,J=6.5 Hz), 4.22(dd,1H,J$_1$=5.5 Hz,J$_2$=9.5 Hz)

The following compounds were obtained in the same manner.
γ-Glu-Val-GABA (Compound 30)
  m.p.: 204°-206 °C. (Decomposition)
  $[\alpha]^{25} = -23.8$ (c=1.0, H$_2$O)
  NMR(0.1NDCl/D$_2$O): $\delta = 0.92$(d,3H,J=7.0 Hz), 0.94(d,3H,J=7.0 Hz), 1.80(tt,2H,J$_1$=7.0 Hz,J$_2$=7.0 Hz), 2.04(dqq,1H,J$_1$=7.0 Hz,J$_2$=7.0 Hz,J$_3$=7.0 Hz), 2.12-2.26(m,2H), 2.40(t,2H,J=7.0 Hz), 2.52(dt,1H,J$_1$=7.5 Hz,J$_2$=16.0 Hz), 2.59(ddd,1H,J$_1$=7.0 Hz,J$_2$=8.0 Hz,J$_3$=16.0 Hz), 3.22(dt,1H,J$_1$=7.0 Hz,J$_2$=13.5 Hz), 3.99(d,1H,J=7.0 Hz), 4.00(t,1H,J=7.0 Hz)

δ-Glu-Hyp-GABA (Compound 31)
  m.p.: 88 °C. (Decomposition)
  $[\alpha]^{25} = -50.3$ (c=1.0, H$_2$O)
  NMR(0.1NDCl/D$_2$O): $\delta = 1.80$(tt,2H,J$_1$=7.0 Hz,J$_2$=7.0 Hz), 2.02-2.09(m,1H), 2.13-2.36(m,1H), 2.41(t,2H,J=7.0 Hz), 2.55-2.77(m,2H), 3.18-3.30(m,2H), 3.62(dd,1H,J$_1$=2.0 Hz,J$_2$=11.0 Hz), 3.79(dd,1H,J$_1$=4.0 Hz,J$_2$=11.0 Hz), 4.09(t,1H,J=7.5 Hz), 4.43(dd,1H,J$_1$=8.0 Hz,J$_2$=8.5 Hz), 4.55-4.60(m,1H)

EXAMPLE 8

(i) To a mixture of 3.98 g of His.H$_2$O.HCl and 2.01 g of sodium carbonate in a mixture of 25 ml of DMF and 50 ml of H$_2$O, 7.27 g of Z-Glu(ONSu)-OBzl in 25 ml of acetonitrile was added at room temperature with stirring. After stirring for 20 hrs, the solvent was distilled and the residue was neutralized with 20 ml of 1N HCl aqueous solution at 5 °C. The precipitated oil was extracted with ml of chloroform and crystalline product was obtained as a precipitate. The resulting product was collected and washed with water and recrystallized from methanol aqueous solution to give 6.34 g of Z-Glu(His-OH)-OBzl; yield 80%.

m.p.: 134°–136 °C.

[α]$^{24}$ = −7.2 (c=1.0, DMF)

(ii) 2.47 g of DCC in 50 ml of dichloromethane was added to a mixture of 5.09 g of Z-Glu(His-OH)-OBzl, 4.02 g of TosOH.GABA-OBzl, 1.11 g of NMM and 2.15 g of HONB in 100 ml of dichloromethane at 0 °C. The mixture was stirred at 0 °C. for 2 hrs and at room temperature for 20 hrs. Precipitated DCUrea and TosOH.NMM were filtered off and the filtrate was evaporated in vacuo. The oily residue was dissolved in 100 ml of chloroform, and the solution was washed with water, 5% sodium hydrogencarbonate aqueous solution, water, 10% citric acid aqueous solution and water. The solvent was distilled and the oily residue was crystallized from ether. The crude product was purified with silica gel column chromatography to give 4.87 g of Z-Glu(His-GABA-OBzl)-OBzl; yield 71%.

m.p.: 139°–141 °C.

[α]$^{24}$ = −10.8 (c=1.1, DMF)

(iii) In the same manner as Example 6 (iv), 4.1 g of Z-Glu(His-GABA-OBzl)-OBzl was hydrogenated in the presence of Pd-C and removed the protecting group to give 1.57 g of γ-Glu-His-GABA (Compound 32).

m.p.: 146°–149 °C. (Decomposition)

[α]$^{25}$ = −3.0 (c=1.0, H$_2$O)

NMR(0.1NDCl/D$_2$O): δ=1.73(tt,2H,J$_1$=7.5 Hz,J$_2$=7.5 Hz), 2.14–2.27(m,2H), 2.32(t,2H,J=7.5 Hz), 2.48(t,2H,J=8.0 Hz), 3.14(dd,1H,J$_1$=8.0 Hz,J$_2$=15.0 Hz), 3.17–3.27(m,3H), 3.87(t,1H,J=6.5 Hz), 4.60(dd,1H,J$_1$=7.0 Hz,J$_2$=8.0 Hz), 7.32(s,1H), 8.65(s,1H)

EXAMPLE 9

(i) 2.03 g of TEA was added to a mixture of 5.84 g of Boc-Phe-OH and 7.03 g of TosOH.β-Ala-OBzl in 80 ml of dichloroethane. 4.54 g of DCC was added to the solution at 0 °C. After stirring for 3 hrs at 0 °C. and overnight at room temperature, precipitated DCUrea was filtered off and the solvent was distilled in vacuo. The residue was dissolved in ethyl acetate and the solution was washed with 10% citric acid aqueous solution, water, 5% sodium hydrogencarbonate aqueous solution and brine. After dehydration over sodium sulfate anhydride, the solvent was evaporated to give 8.36 g of Boc-Phe-β-Ala-OBzl; yield 98%.

(ii) 33 ml of 6N HCl/dioxane was added to a solution of 4.26 g of Boc-Phe-β-Ala-OBzl in 16 ml of dioxane. After stirring for 1 hr at room temperature, the solvent was distilled in vacuo and the residue was dissolved in chloroform. The solution was neutralized with an ice cooled saturated aqueous solution of sodium hydrogencarbonate aqueous solution. The water layer was extracted with chloroform. The procedure was repeated three times, and the chloroform layer was washed with brine. After dehydration over sodium sulfate anhydride, the solvent was distilled in vacuo. The residue was dissolved in 80 ml of dichloromethyl and 3.71 g of Z-Glu-OBzl was added to the solution. The solution was stirred for 3 hrs at 0 °C. and overnight at room temperature. Precipitated DCUrea was filtered off and the filtrate was evaporated in vacuo to give 5.37 g of Z-Glu(Phe-β-Ala-OBzl)-OBzl; yield 77%.

m.p.: 161°–162.5 °C.

[α]$^{22}$ = −12.0 (c=1.0, CHCl$_3$)

The following compounds were obtained in the same manner.

Z-Glu(Phe-GABOB-OBzl)-OBzl m.p.: 142.5°–143.5 °C.

[α]$^{22}$ = −7.2 (c=1.0, CHCl$_3$)

Z-Glu(Phe-EACA-OBzl)-OBzl m.p.: 145°–146 °C.

[α]$^{22}$ = −10.8 (c=1.4, CHCl$_3$)

Z-Glu(Pro-β-Ala-OBzl)-OBzl m.p.: 109°–110.5 °C.

[α]$^{22}$ = −57.2 (c=1.2, CHCl$_3$)

Z-Glu(Pro-GABOB-OBzl)-OBzl m.p.: oily substance

[α]$^{26}$ = −44.9 (c=1.2, CHCl$_3$)

Z-Glu(Pro-EACA-OBzl)-OBzl m.p.: oily substance

[α]$^{22}$ = −40.4 (c=2.0, CHCl$_3$)

Z-Glu(OBzl)-Phe-β-Ala-OBzl m.p.: 157°–158 °C.

[α]$^{22}$ = −20.1 (c=1.0, CHCl$_3$)

Z-Glu(OBzl)-Pro-GABA-OBzl m.p.: 142.5°–143.5 °C.

Z-Glu(OBzl)-Pro-EACA-OBzl m.p.: oily substance

Z-Asp(Phe-β-Ala-OBzl)-OBzl m.p.: 158°–159 °C.

[α]$^{22}$ = −2.2 (c=1.0, CHCl$_3$)

Z-Asp(Phe-EACA-OBzl)-OBzl m.p.: 133°–133.5 °C.

[α]$^{22}$ = +18.9 (c=1.1, CHCl$_3$)

Z-Asp(OBzl)-Phe-β-Ala-OBzl m.p.: 144°–145 °C.

[α]$^{22}$ = +10.7 (c=1.0, CHCl$_3$)

(iii) In the same manner as Example 6 (iv), 2.50 g of Z-Glu(Phe-β-Ala-OBzl)-OBzl was hydrogenated in the presence of Pd-C and removed the protecting group to give 1.30 g of γ-Glu-Phe-β-Ala (Compound 33); yield 99%.

NMR(0.1NDCl/D$_2$O): δ=2.07(dt,1H,J$_1$=7.0 Hz,J$_2$=14.5 Hz), 2.14(dt,1H,J$_1$=7.0 Hz,J$_2$=14.5 Hz), 2.36(ddd,1H,J$_1$=5.5 Hz,J$_2$=8.0 Hz,J$_3$=17.5 Hz), 2.45(ddd,1H,J$_1$=5.5 Hz,J$_2$=6.0 Hz,J$_3$=17.5 Hz), 2.52(t,2H,J=7.0 Hz), 2.99(dd,1H,J$_1$=8.0 Hz,J$_2$=13.5 Hz), 3.03(dd,1H,J$_1$=8.0 Hz,J$_2$=13.5 Hz), 3.27(ddd,1H,J$_1$=5.5 Hz,J$_2$=8.0 Hz,J$_3$=14.0 Hz), 3.40(ddd,1H,J$_1$=5.5 Hz,J$_2$=6.5 Hz,J$_3$=14.0 Hz), 3.97(t,1H,J=6.5 Hz), 4.49(t,1H,J=8.0 Hz), 7.24(dt,2H,J$_1$=1.5 Hz,J$_2$=7.0 Hz), 7.30(tt,1H,J$_1$=1.5 Hz,J$_2$=7.0 Hz), 7.35(tt,2H,J$_1$=1.5 Hz,J$_2$=7.0 Hz)

The following compounds were obtained in the same manner.

γ-Glu-Phe-GABOB (Compound 34)

m.p.: 163°–165 °C. (Decomposition)

[α]$^{26}$ = +21.3 (c=1.0, 0.1NHCl)

NMR(0.1NDCl/D$_2$O): δ=2.09–2.19(m,2H), 2.19–2.27(m,1H), 2.31–2.33(m,1H), 2.30(br.t,2H,J=6.5 Hz), 3.00–3.14(m,2H), 3.14–3.35(m,2H), 3.91–4.03(m,2H), 4.51–4.55(m,1H), 7.20–7.39(m,5H)

γ-Glu-Phe-EACA (Compound 35)

m.p.: 184°–185 °C. (Decomposition)

[α]$^{26}$ = +14.1 (c=1.1, 0.1NHCl)

δNMR(0.1NDCl/D$_2$O): δ=1.07(br.tt,2H,J$_1$=7.0 Hz,J$_2$=7.0 Hz), 1.27(br.tt,2H,J$_1$=7.0 Hz,J$_2$=7.0 Hz), 1.50(br.tt,2H,J$_1$=7.0 Hz,J$_2$=7.0 Hz), 2.12(dt,2H,J$_1$=6.5 Hz,J$_2$=7.5 Hz), 2.33(t,2H,J=7.5 Hz), 2.49(br.t,2H,J=7.5 Hz), 2.99(ddd,1H,J$_1$=6.5 Hz,J$_2$=7.0 Hz,J$_3$=13.5 Hz), 3.01(d,2H,J=8.0 Hz), 3.14(ddd,1H,J$_1$=6.5 Hz,J$_2$=7.0 Hz,J$_3$=13.5 Hz), 4.00(t,1H,J=6.5 Hz), 4.48(t,1H,J=8.0 Hz), 7.26(br.d,2H,J=7.0 Hz), 7.30(br.t,1H,J=7.0 Hz), 7.37(br.t,2H,J=7.0 Hz)

γ-Glu-Pro-β-Ala (Compound 36)

m.p.: 91°-93° C.
[α]²⁶ = +50.1 (c=1.1, 0.1NHCl)
NMR(0.1NDCl/D₂O): δ=1.85-2.05(m,4H), 2.15-2.30(m,3H), 2.62(t,1H,J=6.5 Hz), 2.68(br.t,1H,J=7.5 Hz), 3.39-3.53(m,4H), 3.55-3.70(m,4H), 4.10(t,1H,J=6.5 Hz), 4.32(dd,1H,J₁=4.5 Hz,J₂=8.0 Hz)

γ-Glu-Pro-GABOB (Compound 37)
m.p.: 66°-68° C.
[α]²⁶ = −32 0 (c=1.2, 0.1NHCl)
NMR(0.1NDCl/D₂O): δ=1.90-2.04(m,3H), 2.15-2.33(m,3H), 2.42-2.51(m,1H), 2.57-2.64(m,1H), 2.69(br.t,2H,J=7.0 Hz), 3.31-3.35(m,2H), 3.59-3.68(m,2H), 4.08-4.20(m,2H), 4.15(dd,1H,J₁=5.0 Hz,J₂=9.0 Hz)

γ-Glu-Pro-EACA (Compound 38)
m.p.: 62-°63° C.
[α]²⁶ = −40 5 (c=1.1, 0.1NHCl)
NMR(0.1NDCl/D₂O): δ=1.27-1.36(m,2H), 1.46-1.65(m,4H), 1.86-2.03(m,3H), 2.15-2.30(m,3H), 2.38(t,2H,J=7.5 Hz), 2.68(dt,2H,J₁=3.0 Hz,J₂=8.0 Hz), 3.11-3.26(m,2H), 3.58-3.68(m,2H), 4.13(t,1H,J=7.0 Hz), 4.32(dd,1H,J₁=5.0 Hz,J₂=8.5 Hz)

Glu-Phe-β-Ala (Compound 39)
m.p. 154°-155.5° C.
[α]²⁶ = +35.6 (c=0.9, 0.1NHCl)
NMR(0.1NDCl/D₂O): δ=2.15(dt,2H,J₁=7.5 Hz,J₂=8.0 Hz), 2.28(ddd,1H,J₁=5.5 Hz,J₂=8.0 Hz,J₃=17.0 Hz), 2.41(ddd,1H,J₁=5.5 Hz,J₂=6.5 Hz,J₃=17.0 Hz), 2.51(t,2H,J=7.5 Hz), 2.99(dd,1H,J₁=9.0 Hz,J₂=13.0 Hz), 3.12(dd,1H,J₁=7.0 Hz,J₂=13.0 Hz), 3.20(ddd,1H,J₁=5.5 Hz,J₂=8.0 Hz,J₃=13.5 Hz), 3.39(ddd,1H,J₁=5.5 Hz,J₂=6.5 Hz,J₃=13.5 Hz), 4.07(t,1H,J=6.5 Hz), 4.52(dd,1H,J₁=7.0 Hz,J₂=9.0 Hz), 7.26(br.t,2H,J=7.2 Hz), 7.30(br.t,1H,J=7.2 Hz), 7.37(br.t,2H,J=7.2 Hz)

Glu-Pro-GABA (Compound 40)
m.p.: 157°-158° C.
[α]²⁶ = −60.1 (c=1.0, H₂O)

Glu-Pro-EACA (Compound 41)
m.p.: 76°-78° C. (Decomposition)
[α]²⁶ = −62 8 (c=1.0, 0.1NHCl)
NMR(0.1NDCl/D₂O): δ=1.23-1.33(m,2H), 1.42-1.65(m,4H), 1.79-2.07(m,3H), 2.17-2.31(m,2H), 2.14(dd,1H,J₁=7.0 Hz,J₂=14.5 Hz), 2.34(t,2H,J=7.5 Hz), 2.58(t,2H,J=7.5 Hz), 3.10(dd,1H,J₁=6.5 Hz,J₂=14.0 Hz), 3.24(dd,1H,J₁=7.0 Hz,J₂=14.0 Hz), 3.55-3.65(m,1H), 3.65-3.75(m,1H), 4.36(dd,1H,J₁=7.0 Hz,J₂=8.0 Hz), 4.41(dd,1H,J₁=5.0 Hz,J₂=7.0 Hz)

β-Asp-Phe-β-Ala (Compound 42)
m.p.: 158°-160° C. (Decomposition)
[α]²⁶ = +13.4 (c=1.2, 0.1NHCl)
NMR(0.1NDCl/D₂O): δ2.35(ddd,1H,J₁=5.5 Hz,J₂=8.0 Hz,J₃=17.0 Hz), 2.44(ddd,1H,J₁=5.5 Hz,J₂=6.0 Hz,J₃=17.0 Hz), 3.00(dd,1H,J₁=5.5 Hz,J₂=9.5 Hz), 3.02(d,2H,J=8.0 Hz), 3.04(dd,1H,J₁=5.5 Hz,J₂=9.5 Hz), 3.27(ddd,1H,J₁=5.5 Hz,J₂=8.0 Hz,J₃=14.0 Hz), 3.40(ddd,1H,J₁=5.5 Hz,J₂=6.0 Hz,J₃=14.0 Hz), 4.33(t,1H,J=5.5 Hz), 4.54(t,1H,J=8.0 Hz), 7.23(dt,2H,J₁=1.5 Hz,J₂=6.5 Hz), 7.32(tt,1H,J₁=1.5 Hz,J₂=6.5 Hz), 7.36(tt,2H,J₁=1.5 Hz,J₂=6.5 Hz)

β-Asp-Phe-EACA (Compound 43)
m.p.: 178°-180° C. (Decomposition)
[α]²⁶ = +10.0 (c=1.1, 0.1NHCl)
NMR(0.1NDCl/D₂O): δ=0.97-1.10(m,2H), 1.20-1.35(m,2H), 1.49(tt,2H,J₁=7.5 Hz,J₂=7.5 Hz), 2.32(br.t,2H,J=7.5 Hz), 2.94(dd,1H,J₁=13.0 Hz,J₂=14.0 Hz), 2.99(dd,1H,J₁=8.0 Hz,J₂=18.0 Hz), 3.00(dd,1H,J₁=9.0 Hz,J₂=13.5 Hz), 3.07(dd,1H,J₁=5.5 Hz,J₂=18.0 Hz), 3.10(dd,1H,J₁=7.0 Hz,J₂=13.5 Hz), 3.12(dd,1H,J₁=13.0 Hz,J₂=14.0 Hz), 4.34(dd,1H,J₁=5.5 Hz,J₂=8.0 Hz), 4.52(dd,1H,J₁=7.0 Hz,J₂=9.0 Hz), 7.27(br.t,2H,J=7.0 Hz), 7.31(br.t,1H,J=7.0 Hz), 7.37(br.t,2H,J=7.0 Hz)

Asp-Phe-β-Ala (Compound 44)
m.p.: 168°-171° C. (Decomposition)
[α]²⁶ = +14.9 (c=1.0, 0.1NHCl)
NMR(0.1NDCl/D₂O): δ=2.31(ddd,1H,J₁=5.5 Hz,J₂=8.0 Hz,J₃=17.0 Hz), 2.41(td,1H,J₁=5.5 Hz,J₂=17.0 Hz), 2.99(dd,1H,J₁=7.2 Hz,J₂=18.0 Hz), 3.01(dd,1H,J₁=8.0 Hz,J₂=16.0 Hz), 3.07(dd,1H,J₁=5.0 Hz,J₂=18.0 Hz), 3.10(dd,1H,J₁=7.0 Hz,J₂=16.0 Hz), 2.22(ddd,1H,J₁=5.5 Hz,J₂=8.0 Hz,J₃=14.0 Hz), 3.39(dt,1H,J₁=5.5 Hz,J₂=14.0 Hz), 4.33(dd,1H,J₁=5.0 Hz,J₂=7.2 Hz), 4.53(br.t,1H,J=8.0 Hz), 7.25(d,2H,J=7.0 Hz), 7.31(t,1H,J=7.0 Hz), 7.37(t,2H,J=7.0 Hz)

EXAMPLE 10

(i) To an ice cooled solution of 10.76 g of Boc-Pro-OH and 5.06 g of TEA in 250 ml of THF, 5.43 g of ECF was added dropwise at −15° C. The mixture was stirred at the temperature for 15 min. A solution of 20.1 g of TosOH.GABA-OBzl and 5.57 g of TEA in 100 ml of chloroform was added to the mixture at 0° C. The mixture was stirred at 0° C. for 2 hrs and at room temperature for 20 hrs. The solvent was evaporated and residue was dissolved in 150 ml of ethyl acetate and the solution was washed with water, 5% sodium hydrogencarbonate aqueous solution, brine, 10% citric acid aqueous solution and brine. The organic layer was dried over sodium sulfate anhydride and evaporated in vacuo to give oily Boc-Pro-GABA-OBzl.

The resulting Boc-Pro-GABA-OBzl was treated with 250 ml of 4N HCl/dioxane at room temperature for 2 hrs. The solvent and HCl were distilled in vacuo. The residue was dissolved in 100 ml of dioxane and remaining HCl was coevaporated off with the solvent. The oily residue was crystallized from ethanol/petroleum ether to give 15.48 g of HCl.Pro-GABA-OBzl; yield 95%.

(ii) Using HCl.Pro-GABA-OBzl and Z-Glu(ONSu)-OBzl, the condensation and reduction were carried out in the same manner as Example 6 (iii) and (iv) to give γ-Glu-Pro-GABA (Compound 23).

EXAMPLE 11

(i) To an ice cooled solution of 8.93 g of Z-Leu-OH.DCHA and 8.66 g of TosOH.EACA-OBzl in 100 ml of dichloromethane, 4.22.g of WSCD.HCl was added with stirring. After stirring for 2 hrs at 0° C. and 20 hrs at room temperature, precipitated DCHA.-TosOH was filtered off and the filtrate was evaporated in vacuo. The oily residue was dissolved in 100 ml of ethyl acetate and the solution was washed with water, 5% sodium hydrogencarbonate aqueous solution, brine, 10% citric acid aqueous solution, and brine. After dehydration over sodium sulfate anhydride, the solvent was distilled in vacuo. The oily residue was crystallized from petroleum ether to give 7.51 g of Z-Leu-EACA-OBzl; yield 80%.

Z-Leu-EACA-OBzl
  m.p.: 88°–89 °C.
  $[\alpha]^{25} = -5.1$ (c=1.0, DMF)

The following compounds were obtained in the same manner.

Z-Ile-EACA-OH
  m.p.: 124°–125 °C.
  $[\alpha]^{25} = +5.7$ (c=1.0, DMF)

Z-Pyr-EACA-OH
  m.p.: 105°–106 °C.
  $[\alpha]^{25} = +7.3$ (c=1.0, DMF)

Z-Gly-β-Ala-OBzl
  m.p.: 81°–82 °C.

Z-Ala-β-Ala-OBzl
  m.p.: 92°–93 °C.
  $[\alpha]^{25} = +6.8$ (c=1.0, DMF)

Z-Val-β-Ala-OBzl
  m.p.: 116°–117 °C.
  $[\alpha]^{25} = +9.4$ (c=1.0, DMF)

Z-Leu-β-Ala-OBzl
  m.p.: 75°–76 °C.
  $[\alpha]^{25} = -3.2$ (c=1.0, DMF)

Z-Ser-β-Ala-OBzl
  m.p.: 101.5°–102.5 °C.
  $[\alpha]^{25} = +5.5$ (c=1.0, DMF)

Z-Thr-β-Ala-OBzl
  m.p.: 85°–87 °C.
  $[\alpha]^{25} = +5.9$ (c=1.0, DMF)

Z-Hyp-β-Ala-OBzl
  m.p.: 99°–100 °C.
  $[\alpha]^{25} = -18.0$ (c=1.0, DMF)

Z-Asp(OBzl)-β-Ala-OBzl
  m.p.: 91°–92 °C.
  $[\alpha]^{25} = -5.6$ (c=1.0, DMF)

Z-Pyr-β-Ala-OBzl
  m.p.: 91°–92 °C.
  $[\alpha]^{25} = +2.1$ (c=1.0, DMF)

Z-Lys(Z)-GABA-OBzl
  m.p.: 116°–118 °C.
  $[\alpha]^{25} = -3.1$ (c=1.0, DMF)

Z-Asp(GABA-OBzl)-OBzl
  m.p.: 105°–107 °C.
  $[\alpha]^{25} = -8.5$ (c=1.0, DMF)

Z-Trp-GABA-OBzl
  m.p.: amorphous substance

Z-Glu(OBzl)-GABA-OBzl
  m.p.: 87°–89 °C.
  $[\alpha]^{24} = -1.9$ (C=1.0, DMF)

Z-Ile-β-Ala-OBzl
  m.p.: 122°–123 °C.
  $[\alpha]^{24} = +6.9$ (C=1.0, DMF)

Z-Tyr(Bzl)-β-Ala-OBzl
  m.p.: 147°–148 °C.
  $[\alpha]^{24} = -11.9$ (C=1.0, DMF)

Z-Gly-GABOB-OBzl
  m.p.: 113°–115 °C.

Z-Ala-GABOB-OBzl
  m.p. 101°–103 °C.
  $[\alpha]^{24} = +5.5$ (C=1.0, DMF)

Z-Val-GABOB-OH
  m.p.: 138°–139 °C.
  $[\alpha]^{24} = +11.3$ (C=1.0, DMF)

Z-Ser-GABOB-OBzl
  m.p.: 118°–119 °C.
  $[\alpha]^{24} = +2.5$ (C=1.0, DMF)

Z-Thr-GABOB-OBzl
  m.p.: 79°–81 °C.
  $[\alpha]^{24} = +4.2$ (C=1.0, DMF)

Z-Hyp-GABOB-OBzl
  m.p.: oily substance

Z-Asp(OBzl)-GABOB-OBzl
  m.p.: 98°–99 °C.
  $[\alpha]^{24} = -10.3$ (C=1.0, DMF)

Z-Glu(GABOB-OBzl)-OBzl
  m.p.: 104°–105 °C.
  $[\alpha]^{24} = -8.3$ (C=1.0, DMF)

Z-Tyr(Bzl)-GABOB-OBzl
  m.p.: 133°–134 °C.
  $[\alpha]^{24} = -11.9$ (C=1.0, DMF)

Z-Gly-EACA-OBzl
  m.p.: 79°–80° C.

Z-Ala-EACA-OBzl
  m.p.: 65°–66 °C.
  $[\alpha]^{24} = +4.6$ (C=1.0, DMF)

Z-Val-EACA-OH
  m.p.: 125°–127 °C.
  $[\alpha]^{24} = +10.2$ (C=1.0, DMF)

Z-Ser-EACA-OBzl
  m.p.: 80°–81 °C.
  $[\alpha]^{24} = +2.0$ (C=1.0, DMF)

Z-Hyp-EACA-OBzl
  m.p.: oily substance

Z-Asp(OBzl)-EACA-OBzl
  m.p.: oily substance

Z-Glu(EACA-OBzl)-OBzl
  m.p.: 77°–78 °C.
  $[\alpha]^{24} = -8.3$ (C=1.0, DMF)

Z-Thr-EACA-OBzl
  m.p.: 84°–85 °C.
  $[\alpha]^{24} = +2.3$ (C=1.0, DMF)

Z-Tyr(Bzl)-EACA-OBzl
  m.p.: 124°–126° C.
  $[\alpha]^{24} = -8.4$ (C=1.0, DMF)

Z-D-Asp(GABA-Bzl)-OBzl(NO$_2$)
  m.p.: 141°–142 °C.
  $[\alpha]^{24} = -8.6$ (C=1.0, DMF)

Boc-D-Asp(OBzl)-GABA-OBzl
  m.p.: 81°–82 °C.
  $[\alpha]^{25} = +10.9$ (c=1.0, DMF)

(ii) In the same manner as Example 1 (ii), 6.0 g of Z-Leu-GABA-OBzl was hydrogenated in the presence of Pd-C and removed the protecting group to give 2.37 g of Leu-EACA·½H$_2$O (Compound 45); yield 73%.
  m.p.: 146°–148 °C.
  $[\alpha]^{25} = +17.0$ (c=1.0, H$_2$O)

The following compounds were obtained in the same manner.

Ile-EACA (Compound 46)
  m.p.: 160°–162 °C.
  $[\alpha]^{25} = +17.8$ (c=1.0, H$_2$O)

Pyr-EACA (Compound 47)
  m.p.: 130°–131 °C.
  $[\alpha]^{25} = -23.2$ (c=1.0, H$_2$O)

Gly-β-Ala (Compound 48)
  m.p.: 226°–227 °C. (Decomposition)
  NMR(0.1NDCl/D$_2$O): δ=2.56(t,2H,J=6.5 Hz), 3.49(t,2H,J=6.5 Hz), 3.77(s,2H)

Ala-β-Ala (Compound 49)
  m.p.: 225°–226 °C. (Decomposition)
  $[\alpha]^{25} = +16.3$ (c=1.0, H$_2$O)
  NMR(0.1NDCl/D$_2$O): δ=1.49(d,3H,J=7 Hz), 2.61(t,2H,J=6.5 Hz), 3.46(dt,1H,J$_1$=6.5 Hz,J$_2$=14.0 Hz), 3.54(dt,1H,J$_1$=6.5 Hz,J$_2$=14.0 Hz), 4.02(q,1H,J=7.0 Hz)

Val-β-Ala (Compound 50)
  m.p.: 245°-246 °C. (Decomposition)
  $[\alpha]^{25} = +37.5$ (c=1.0, H$_2$O)
Leu-β-Ala (Compound 51)
  m.p.: 218°-220 °C.
  $[\alpha]^{25} = +34.6$ (c=1.0, H$_2$O)
Ser-β-Ala (Compound 52)
  m.p.: 206°-208 °C. (Decomposition)
  $[\alpha]^{25} = +15.0$ (c=1.0, H$_2$O)
  NMR(0.1NDCl/D$_2$O): δ=2.55(t,2H,J=6.5 Hz), 3.49(t,2H,J=6.5 Hz), 3.89(dd,1H,J$_1$=6.0 Hz,J$_2$=12.5 Hz), 3.96(dd,1H,J$_1$=4.0 Hz,J$_2$=12.5 Hz), 4.08(dd,1H,J$_1$=4.0 Hz,J$_2$=6.0 Hz)
Thr-β-Ala (Compound 53)
  m.p.: 199°-201 °C. (Decomposition)
  $[\alpha]^{25} = +14.4$ (c=1.0, H$_2$O)
  NMR(0.1NDCl/D$_2$O): δ=1.27(d,3H,J=7.0 Hz), 2.55(t,2H,J=6.5 Hz), 3.46(dt,1H,J$_1$=6.5 Hz,J$_2$=13.0 Hz), 3.52(dt,1H,J$_1$=6.5 Hz,J$_2$=13.0 Hz), 3.79(d,1H,J=7.0 Hz), 4.10(dq,1H,J$_1$=7.0 Hz,J$_2$=7.0 Hz)
Hyp-β-Ala (Compound 54)
  m.p 222°-224 °C. (Decomposition)
  $[\alpha]^{25} = -39.8$ (c=1.0, H$_2$O)
Asp-β-Ala (Compound 55)
  m.p.: 203°-205 °C. (Decomposition)
  $[\alpha]^{25} = +13.9$ (c=1.0, 0.5NNaOH)
  NMR(0.1NDCl/D$_2$O): δ=2.60(t,2H,J=6.5 Hz), 2.96(dd,1H,J$_1$=7.0 Hz,J$_2$=18.0 Hz), 3.01(dd,1H,J$_1$=5.5 Hz,J$_2$=18.0 Hz), 3.44(dt,1H,J$_1$=6.5 Hz,J$_2$=14.0 Hz), 3.56(dt,1H,J$_1$=6.5 Hz,J$_2$=14.0 Hz), 4.29(dd,1H,J$_1$=5.5 Hz,J$_2$=7.0 Hz)
Pyr-β-Ala (Compound 56)
  m.p.: 206°-208° C.
  $[\alpha]^{25} = -25.8$ (c=1.0, H$_2$O)
  NMR(0.1NDCL/D$_2$O): δ=2.09-1.99(M,1H), 2.57-2.33(m,3H), 2.61(t,2H,J=6.5 Hz), 3.47(ddd,1H,J$_1$=6.5 Hz,J$_2$=6.5 Hz,J$_3$=14.0 Hz), 3.51(ddd,1H,J$_1$=6.5 Hz,J$_2$=6.5 Hz,J$_3$=14.0 Hz), 4.28(dd,1H,J$_1$=5.0 Hz,J$_2$=9.0 Hz)
Lys-GABA (Compound 57)
  NMR(0.1NDCl/D$_2$O): δ=1.49-1.40(m,2H), 1.76-1.67(m,2H), 1.83(tt,2H,J$_1$=7.0 Hz,J$_2$=7.0 Hz), 1.95-1.87(m,2H), 2.41(t,2H,J=7.0 Hz), 300(br.t,2H,J=7.0 Hz), 3.25(dt,1H,J=7.5 Hz), 3.25(dt,1H,J$_1$=7.0 Hz,J$_2$=14.0 Hz), 3.30(dt,1H,J$_1$=7.0 Hz,J$_2$=14.0 Hz), 3.90(t,1H,J=6.5 Hz)
β-Asp-GABA (Compound 58)
  m.p.: 205°-207° C. (Decomposition)
  $[\alpha]^{25} = -14.7$ (c=0.5, 0.1NNaOH)
Trp-GABA (Compound 59)
  m.p.: 79°-81° C. (amorphous substance)
  $[\alpha]^{24} = +51.5$ (C=1.0, H$_2$O)
Glu-GABA (Compound 60)
  m.p.: 146°-147° C. (Decomposition)
  $[\alpha]^{24} = +36.1$ (C=1.0, H$_2$O)
Ile-β-Ala (Compound 61)
  m.p.: 228°-230° C. (Decomposition)
  $[\alpha]^{24} = +31.8$ (C=1.0, H$_2$O)
Tyr-β-Ala (Compound 62)
  m.p.: 251°-253° C. (Decomposition)
  $[\alpha]^{24} = +22.3$ (C=1.0, 0.1NNaOH)
Gly-GABOB (Compound 63)
  m.p.: 222°-223° C. (Decomposition)
Ala-GABOB (Compound 64)
  m.p.: 225°-226° C. (Decomposition)
  $[\alpha]^{24} = +28.5$ (C=1.0, H$_2$O)
Val-GABOB (Compound 65)
  m.p.: 208°-210° C. (Decomposition)
  $[\alpha]^{24} = +47.5$ (C=1.0, H$_2$O)
Ser-GABOB (Compound 66)
  m.p.: 205°-207° C. (Decomposition)
  $[\alpha]^{24} = +17.5$ (C=1.0, H$_2$O)
Thr-GABOB.H$_2$O (Compound 67)
  m.p.: 190°-191° C. (Decomposition)
  $[\alpha]^{24} = +34.0$ (C=1.0, H$_2$O)
Hyp-GABOB (Compound 68)
  m.p.: 219°-220° C. (Decomposition)
  $[\alpha]^{24} = -23.2$ (C=1.0, H$_2$O)
Asp-GABOB (Compound 69)
  m.p.: 168°-170° C. (Decomposition)
  $[\alpha]^{24} = -17.7$ (C=1.0, H$_2$O)
γ-Glu-GABOB (Compound 70)
  m.p.: 176°-178° C. (Decomposition)
  $[\alpha]^{24} = +6.3$ (C=1.0, H$_2$O)
Tyr-GABOB (Compound 71)
  m.p.: 75° C. (amorphous substance)
  $[\alpha]^{24} = +33.9$ (C=1.0, H$_2$O)
Gly-EACA (Compound 72)
  m.p.: 197°-198° C.
Ala-EACA (Compound 73)
  m.p.: 163°-164° C.
  $[\alpha]^{24} = +5.9$ (C=1.0, H$_2$O)
Val-EACA (Compound 74)
  m.p.: 146°-148° C.
  $[\alpha]^{24} = +22.6$ (C=1.0, H$_2$O)
Ser-EACA (Compound 75)
  m.p.: 179°-181° C.
  $[\alpha]^{24} = +8.9$ (C=1.0, H$_2$O)
Hyp-EACA (Compound 76)
  m.p.: 202°-203° C. (Decomposition)
  $[\alpha]^{24} = -36.8$ (C=1.0, H$_2$O)
Asp-EACA (Compound 77)
  m.p.: 217°-218° C. (Decomposition)
  $[\alpha]^{24} = +11.1$ (C=1.0, 0.1NNaOH)
γ-Glu-EACA (Compound 78)
  m.p.: 201°-202° C. (Decomposition)
  $[\alpha]^{24} = +8.5$ (C=1.0, 0.1NNaOH)
β-D-Asp-EACA (Compound 79)
  m.p.: 212°-213° C. (Decomposition)
  $[\alpha]^{24} = +15.6$ (C=1.0, 0.1NNaOH)
In the same manner as Method ](3), D-Asp-GABA (Compound 80) was obtained.
  m.p.: 212°-213.5° C. (Decomposition)
  $[\alpha]^{25} = -12.5$ (c=0.5, 0.1NNaOH)

EXAMPLE 12

(i) HCl.Phe-GABA-OBzl was obtained in the same manner as Example 9 (i) and (ii). 2.11 g of WSCD.HCl was added to the mixture of 3.57 g of Z-Asp(OBzl)-OH, 4.15 g of HCl.Phe-GABA-OBzl and 1.11 g of TEA in an ice cooled water. The reaction mixture was stirred at 0° C. for 2 hrs and at room temperature for 20 hrs, and washed with water, 10% citric acid aqueous solution, water, 5% sodium hydrogencarbonate aqueous solution and brine. After dehydration over sodium sulfate anhydride, the solvent was distilled in vacuo and crystal was collected from ether to give 5.31 g of Z-Asp(OBzl)-Phe-GABA-OBzl; yield 78%.
  m.p.: 128°-130° C.
  $[\alpha]^{25} = -30.2$ (c=1.0, DMF)

The following compounds were obtained in the same manner.

Z-Asp(Phe-GABA-OBzl)-OBzl
  m.p.: 163°-165° C.
  $[\alpha]^{25} = -55.4$ (c=1.0, DMF)

Z-Glu(OBzl)-Phe-GABA-OBzl
 m.p.: 129°-131 ° C.
 $[\alpha]^{25} = -16.7$ (c=1.0, DMF)
Z-D-Asp(Phe-GABA-OBzl)-OBzl(NO2)
 m.p.: 149°-151 ° C.
 $[\alpha]^{24} = -8.1$ (C=1.0, DMF)
Z-Asp(Pro-GABA-OBzl)-OBzl
 m.p.: oily substance Z-Asp(OBzl)-Pro-GABA-OBzl
 m.p.: oily substance
Z-Glu(OBzl)-Pro-β-Ala-OBzl
 m.p.: oily substance
Z-Asp(OBzl)-Phe-GABOB-OBzl
 m.p.: 109°-111 ° C.
 $[\alpha]^{24} = -19.5$ (C=1.1, DMF)
Z-Asp(Phe-GABOB-OBzl)-OBzl
 m.p.: 143°-145 ° C.
 $[\alpha]^{24} = -9.9$ (C=1.1, DMF)
Z-D-Asp(Phe-GABOB-OBzl)-OBzl(NO$_2$)
 m.p.: 154°-156 ° C.
 $[\alpha]^{24} = -1.5$ (C=1.0, DMF)
Z-Glu(OBzl)-Phe-GABOB-OBzl
 m.p.: 137°-139 ° C.
 $[\alpha]^{24} = -16.4$ (C=1.0, DMF)
Z-Asp(OBzl)-Pro-GABOB-OBzl
 m.p.: oily substance
Z-Asp(Pro-GABOB-OBzl)-OBzl
 m.p.: oily substance
Z-D-Asp(Pro-GABOB-OBzl)-OBzl(NO$_2$)
 m.p.: oily substance
Z-Glu(OBzl)-Pro-GABOB-OBzl
 m.p.: oily substance
Z-Asp(OBzl)-Phe-EACA-OBzl
 m.p.: 131°-133 ° C.
 $[\alpha]^{24} = -20.3$ (C=1.0, DMF)
Z-D-Asp(Phe-EACA-OBzl)-OBzl(NO$_2$)
 m.p.: 156°-158 ° C.
 $[\alpha]^{24} = -2.3$ (C=1.5, DMF)
Z-Glu(OBzl)-Phe-EACA-OBzl
 m.p.: 142°-143 ° C.
 $[\alpha]^{24} = -15.4$ (C=1.4, DMF)
Z-Asp(OBzl)-Pro-EACA-OBzl
 m.p.: oily substance
Z-Asp(Pro-EACA-OBzl)-OBzl
 m.p.: oily substance
Z-D-Asp(Pro-EACA-OBzl)-OBzl(NO$_2$)
 m.p.: oily substance
Boc-D-Asp(OBzl)-Phe-GABA-OBzl
 m.p.: 96°-97 ° C.
 $[\alpha]^{25} = -10.9$ (c=1.0, DMF) ps Boc-D-Asp(OBzl)-Pro-GABA-OBzl
 m.p.: oily substance
Boc-D-Asp(OBzl)-Phe-GABOB-OBzl
 m.p. 106°-108 ° C.
 $[\alpha]^{24} = +1.6$ (C=1.2, DMF)
Boc-D-Asp(OBzl)-Pro-GABOB-OBzl
 m.p.: oily substance
Boc-D-Asp(OBzl)-Phe-EACA-OBzl
 m.p.: 93°-95 ° C.
 $[\alpha]^{24} = -1.3$ (C=1.1, DMF)
Boc-D-Asp(OBzl)-Pro-EACA-OBzl
 m.p.: oily substance (ii) In the same manner as Example 6 (iv), 3.74 g of Z-Asp(OBzl)-Phe-GABA-OBzl was hydrogenated in the presence of Pd-C and removed the protecting group to give 1.39 g of Asp-Phe-GABA (Compound 81); yield 69%.
 m.p.: 217°-218 ° C. (Decomposition)
 $[\alpha]^{25} = +16.0$ (c=1.0, H$_2$O)

β-Asp-Phe-GABA (Compound 82)
 m.p.: 216°-217 ° C. (Decomposition)
 $[\alpha]^{25} = -22.1$ (c=0.5, 0.1NNaOH).
Glu-Phe-GABA (Compound 83)
 m.p.: 196°-198 ° C. (Decomposition)
 $[\alpha]^{25} = -15.2$ (c=0.5, 0.05NNaOH)
β-D-Asp-Phe-GABA (Compound 84)
 m.p.: 190°-192 ° C. (Decomposition)
 $[\alpha]^{24} = -3.2$ (C=1.0, H$_2$O)
β-Asp-Pro-GABA (Compound 85)
 m.p.: 85°-87 ° C. (Decomposition)
 $[\alpha]^{24} = -66.8$ (C=1.0, H$_2$O)
Asp-Pro-GABA (Compound 86)
 m.p.: 55 ° C. (amorphous substance)
 $[\alpha]^{24} = -63.8$ (C=1.0, H$_2$O)
Glu-Pro-β-Ala (Compound 87)
 m.p.: 69°-70 ° C.
 $[\alpha]^{24} = -61.1$ (C=1.0, H$_2$O)
Asp-Phe-GABOB (Compound 88)
 m.p. 198°-200 ° C. (Decomposition)
 $[\alpha]^{24} = +2.6$ (C=0.6, 0.1NNaOH)
 NMR(0.1NDCl/D$_2$O): δ=2.06-2.30(m,2H), 2.95-3.10(m,2H), 2.95-3.30(m,2H), 3.06-3.17(m,1H), 3.20-3.30(m,1H), 3.86-3.96(m,1H), 4.30-4.37(m,1H), 4.54-4.62(m,1H), 7.2-7.4(m,5H)
β-Asp-Phe-GABOB (Compound 89)
 m.p.: 168°-170 ° C. (Decomposition)
 $[\alpha]^{24} = -15.6$ (C=0.7, 0.1NNaOH)
 NMR(0.1NDCl/D$_2$O): δ=2.12-2.33(m,2H), 2.87-2.99(m,2H), 3.00-3.06(m,2H), 3.05-3.30(m,2H), 3.90-4.00(m,1H), 4.17(t,1H,J=5.8 Hz), 4.49-4.57(m,1H), 7.2-7.4(m,5H)
β-D-Asp-Phe-GABOB (Compound 90)
 m.p.: 98°-100 ° C. (Decomposition)
 $[\alpha]^{24} = +5.2$ (C=1.5, H$_2$O)
 NMR(0.1NDCl/D$_2$O): δ=2.12-2.24(m,1H), 2.27-2.35(m,1H), 2.89-2.96(m,2H), 2.99-3.06(m,2H), 3.05-3.16(m,1H), 3.16-3.25(m,1H), 3.90-3.99(m,1H), 4.10-4.16(m,1H), 4.48-4.57(m,1H), 7.2-7.4(m,5H)
Glu-Phe-GABOB (Compound 91)
 m.p.: 220°-222 ° C. (Decomposition)
 $[\alpha]^{24} = +9.1$ (C=0.6, 0.1NNaOH)
 NMR(0.1NDCl/D$_2$O): δ=2.03-2.29(m,2H), 2.10-2.18(m,2H), 2.46-2.54(m,2H), 2.98-3.08(m,1H), 3.10-3.18(m,1H), 3.10-3.30(m,2H), 3.84-3.95(m,1H), 4.04-4.10(m,1H), 4.52-4.61(m,1H), 7.25-7.45(m,5H)
Asp-Pro-GABOB (Compound 92)
 m.p.: oily substance
 $[\alpha]^{24} = -58.6$ (C=1.3, H$_2$O)
 NMR(0.1NDCl/D$_2$O): δ=1.89-2.00(m,2H), 2.10-2.12(m,2H), 2.28-2.39(m,1H), 2.42-2.52(m,1H), 2.57-2.65(m,1H), 2.94(dd,1H,J$_1$=8.8 Hz, J$_2$=18.0 Hz), 3.14(dd,1H,J$_1$=4.0 Hz,J$_2$=18.0 Hz), 3.24-3.41(m,2H), 3.61-3.71(m,1H), 3.71-3.80(m,1H), 4.10-4.21(m,1H), 4.45(dd,1H,J$_1$=6.6 Hz,J$_2$=8.1 Hz), 4.65(dd,1H,J$_1$=4.0 Hz,J$_2$=8.8 Hz)
β-Asp-Pro-GABOB (Compound 93)
 m.p.: oily substance
 $[\alpha]^{24} = -70.5$ (C=1.1, H$_2$O)
 NMR(0.1NDCl/D$_2$O): δ=1.90-2.07(m,3H), 2.23-2.34(m,1H), 2.42-2.52(m,1H), 2.57-2.66(m,1H), 3.17(dd,1H,J$_1$=3.9 Hz,J$_2$=18.1 Hz), 3.26(dd,1H,J$_1$=5.8 Hz,J$_2$=18.1 Hz), 3.30-3.38(m,2H), 3.58-3.68(m,2H), 4.11-4.21(m,1H), 4.34(dd,1H,J$_1$=3.9 Hz,J$_2$=5.8 Hz), 4.39(dd,1H,J$_1$=4.9 Hz,J$_2$=8.9 Hz)
β-D-Asp-Pro-GABOB (Compound 94)
 m.p.: oily substance
 $[\alpha]^{24} = -64.8$ (C=1.1, H$_2$O)

NMR(0.1NDCl/D$_2$O): δ=1.90-2.06(m,3H), 2.22-2.33(m,1H), 2.42-2.53(m,3H), 2.57-2.65(m,1H), 3.20(d,2H,J=4.9 Hz), 3.28-3.40(m,2H), 3.55-3.70(m,2H), 4.10-4.22(m,1H), 4.39(t,1H,J=4.9 Hz), 4.40(dd,1H,J$_1$=4.4 Hz,J$_2$=8.1 Hz)

Glu-Pro-GABOB (Compound 95)
m.p.: oily substance
[α]$^{24}$=−47.1 (C=1.3, H$_2$O)
NMR(0.1NDCl/D$_2$O): δ=1.87-2.13(m,3H), 2.13-2.29(m,2H), 2.29-2.40(m,1H), 2.40-2.53(m,1H), 2.57-2.56(m,1H), 2.58-2.65(m,2H), 3.26-3.42(m,2H), 3.60-3.69(m,1H), 3.73-3.81(m,1H), 4.12-4.21(m,1H), 4.43-4.50(m,1H;Pro-unit), 4.43-4.50(m,1H;Glu-unit)

Asp-Phe-EACA (Compound 96)
m.p.: 179°-181 °C. (Decomposition)
[α]$^{24}$=+3.3 (C=0.7, 0.1NNaOH)
NMR(0.1NDCl/D$_2$O): δ=0.95-1.09(m,2H), 1.20-1.32(m,2H), 1.42-1.53(m,2H), 2.30(t,2H,J=7.2 Hz), 2.89-3.18(m,2H), 2.93-3.18(m,2H;Phe-unit), 2.93-3.18(m,2H;Asp-unit), 4.33(t,1H,J=6.3 Hz), 4.51(t,1H,J=7.9 Hz), 7.2-7.4(m,5H)

β-D-Asp-Phe-EACA (Compound 97)
m.p.: 181°-183 °C. (Decomposition)
[α]$^{24}$=+1.6 (C=0.6, 0.1NNaOH)
NMR(0.1NDCl/D$_2$O): δ=0.98-1.10(m,2H), 1.22-1.33(m,2H), 1.43-1.53(m,2H), 2.31(t,2H,J=7.4 Hz), 2.91-3.00(m,1H), 2.95-3.00(m,2H), 3.00-3.05(m,2H), 3.12(ddd,1H,J$_1$=6.8 Hz,J$_2$=6.8 Hz,J$_3$=13.5 Hz), 4.25(t,1H,J=5.6 Hz), 4.47(t,1H,J=8.0 Hz), 7.2-7.4(m,5H)

Glu-Phe-EACA (Compound 98)
m.p.: 100°-102 °C.
[α]$^{24}$=+8.8 (C=0.7, 0.1NNaOH)
NMR(0.1NDCl/D$_2$O): δ=0.96-1.06(m,2H), 1.20-1.31(m,2H), 1.41-1.52(m,2H), 2.09-2.21(m,2H), 2.30(t,2H,J=7.5 Hz), 2.51(t,2H,J=7.2 Hz), 2.94(ddd,1H,J$_1$=6.8 Hz,J$_2$=6.8 Hz,J$_3$=13.7 Hz), 2.98(dd,1H,J$_1$=9.3 Hz,J$_2$=13.4 Hz), 3.11(ddd,1H,J$_1$=6.8 Hz,J$_2$=6.8 Hz,J$_3$=13.7 Hz;EACA-unit), 3.11(dd,1H,J$_1$=6.8 Hz,J$_2$=6.8 Hz;Phe-unit), 4.08(t,1H,J=6.6 Hz), 4.51(dd,1H,J$_1$=6.8 Hz,J$_2$=9.3 Hz), 7.2-7.4(m,5H)

Asp-Pro-EACA (Compound 99)
m.p.: 141°-143 °C. (Decomposition)
[α]$^{24}$=−60.9 (C=0.6, 0.1NNaOH)
NMR(0.1NDCl/D$_2$O): δ=1.26-1.36(m,2H), 1.45-1.55(m,2H), 1.55-1.65(m,2H), 1.86-1.96(m,1H), 1.96-2.10(m,2H), 2.26-2.36(m,1H), 2.37(t,2H,J=7.4 Hz), 2.94(dd,1H,J$_1$=8.8 Hz,J$_2$=20.2 Hz), 3.13(ddd,1H,J$_1$=6.7 Hz,J$_2$=6.7 Hz,J$_3$=13.5 Hz), 3.16(dd,1H,J$_1$=4.3 Hz,J$_2$=20.0 Hz), 3.26(ddd,1H,J$_1$=6.8 Hz,J$_2$=6.8 Hz,J$_3$=13.5 Hz), 3.63-3.71(m,1H), 3.71-3.79(m,1H), 4.65(dd,1H,J$_1$=4.3 Hz,J$_2$=8.8 Hz)

β-Asp-Pro-EACA (Compound 100)
m.p.: oily substance
[α]$^{24}$=−99.9 (C=1.4, H$_2$O)
NMR(0.1NDCl/D$_2$O) δ=1.27-1.37(m,2H), 1.47-1.56(m,2H), 1.56-1.65(m,2H), 1.87-1.97(m,1H), 1.97-2.04(m,2H), 2.21-2.33(m,1H), 2.38(t,2H,J=7.3 Hz), 3.11-3.28(m,2H), 3.16-3.24(m,2H), 3.54-3.69(m,2H), 4.34(dd,1H,J$_1$=4.4 Hz,J$_2$=8.7 Hz), 4.34-4.38(m,1H)

β-D-Asp-Pro-EACA (Compound 101)
m.p.: oily substance
[α]$^{24}$=−62.1 (C=1.3, H$_2$O)
NMR(0.1NDCl/D$_2$O): δ=1.26-1.37(m,2H), 1.46-1.56(m,2H), 1.56-1.65(m,2H), 1.87-1.97(m,1H), 1.97-2.04(m,2H), 2.21-2.32(m,1H), 2.38(t,2H,J=7.3 Hz), 3.10-3.28(m,2H), 3.16-3.23(m,2H), 3.53-3.70(m,2H), 4.35(dd,1H,J$_1$=4.3 Hz,J$_2$=8.9 Hz), 4.35-4.40(m,1H)

In the same manner as Method ](3), D-Asp-Phe-GABA (Compound 102) was obtained.
m.p.: 187°-189 °C. (Decomposition)
[α]$^{25}$=−19.3 (c=0.5, 0.1NNaOH)

D-Asp-Pro-GABA (Compound 103)
m.p.: 155°-156 °C.
[α]$^{24}$=−67.9 (C=1.0, H$_2$O)

D-Asp-Phe-GABOB (Compound 104)
m.p.: 177°-179 °C. (Decomposition)
[α]$^{24}$=−16.7 (C=0.6, 0.1NNaOH)
NMR(0.1NDCl/D$_2$O): δ=2.28-2.46(m,2H), 2.73(dd,1H,J$_1$=5.9 Hz,J$_2$=15.4 Hz), 2.78(dd,1H,J$_1$=5.9 Hz,J$_2$=15.4 Hz), 2.92-3.03(m,1H), 3.10-3.20(m,1H), 3.15-3.34(m,2H), 3.98-4.07(m,1H), 4.29(t,1H,J=5.9 Hz), 4.61-4.69(m,1H), 7.2-7.4(m,5H)

D-Asp-Pro-GABOB (Compound 105)
m.p.: oily substance
[α]$^{24}$=−64.1 (C=1.3, H$_2$O)
NMR(0.1NDCl/D$_2$O): δ=1.90-2.10(m,3H), 2.24-2.37(m,1H), 2.43-2.53(m,1H), 2.63(dd,1H,J$_1$=4.2 Hz,J$_2$=16.0 Hz), 2.92(dd,1H,J$_1$=8.4 Hz,J$_2$=17.8 Hz), 3.09(dd,1H,J$_1$=4.5 Hz,J$_2$=17.8 Hz), 3.28-3.38(m,2H), 3.64-3.73(m,1H), 3.73-3.82(m,1H), 4.13-4.22(m,1H), 4.43(dd,1H,J$_1$=4.3 Hz,J$_2$=8.9 Hz), 4.66(dd,1H,J$_1$=4.5 Hz,J$_2$=8.4 Hz)

D-Asp-Phe-EACA (Compound 106)
m.p.: 167°-169 °C. (Decomposition)
[α]$^{24}$=−16.3 (C=0.6, 0.1NNaOH)
NMR(0.1NDCl/D$_2$O): δ=1.07-1.18(m,2H), 1.30-1.41(m,2H), 1.45-1.57(m,2H), 2.32(t,2H,J=7.6 Hz), 2.80(d,2H,J=6.0 Hz), 2.93-3.15(m,2H), 2.93-3.22(m,2H), 4.30(t,1H,J=6.0 Hz), 4.57(t,1H,J=8.4 Hz), 7.2-7.4(m,5H)

D-Asp-Pro-EACA (Compound 107)
m.p. 155°-157 °C. (Decomposition)
[α]$^{24}$=−100.6 (C=0.6, 0.1NNaOH)
NMR(0.1NDCl/D$_2$O): δ=1.28-1.39(m,2H), 1.47-1.56(m,2H), 1.56-1.66(m,2H), 1.90-1.99(m,1H), 1.99-2.08(m,2H), 2.24-2.36(m,1H), 2.39(t,2H,J=7.4 Hz), 2.91(dd,1H,J$_1$=8.6 Hz,J$_2$=16.0 Hz), 3.08(dd,1H,J$_1$=3.8 Hz,J$_2$=16.0 Hz), 3.13-3.28(m,2H), 3.63-3.72(m,1H), 3.73-3.81(m,1H), 4.38(dd,1H,J$_1$=4.4 Hz,J$_2$=8.6 Hz), 4.65(dd,1H,J$_1$=3.8 Hz,J$_2$=8.6 Hz)

EXAMPLE 13

In the same manner as Example 8, γ-Glu-5-HTP-GABA (Compound 108) was obtained.
m.p. 120°-123 °C. (Decomposition)
[α]$^{24}$=+12.8 (C=1.0, H$_2$O)

The following descriptions serve to illustrative pharmaceutical studies of the compounds of the present invention.

(I) A neurotropic effect of the peptide compounds of the present invention was examined by the method of Maria-S. Oitzl and J. P. Huston [Brain research, 308, 33–42 (1984)].

Wistar-strain rats were implanted with a set of electrodes for recording EEG under anesthesia with pentobarbital (50 mg/kg, i.p.). The electrodes were bilaterally implanted into the hippocampus (Bregma −2.7 mm, Lateral 2.5 mm, Depth 2.8 mm) by reference to THE RAT BRAIN IN STEREOTAXIC COODINATES (George Paxion & Charles Watson, Academic press). Chemitorode, a injection guide cannula uniting with electrode for recording, was implanted in the temporoparietal left hole. The test drugs were unilaterally injected into the hippocampus of freely moving rats to examine their effect on EEG activity.

The rats were kept for about a week for a cure, and then used for the experiments. After the EEG activity was recorded for dozens of minutes in a normal state, 100 ng to 10 μg of the test drug dissolved in 2 μl of saline was injected into the hippocampus through the injection guide cannula. Only saline was used as a control. Immediately after the administration it began to record the EEG activity.

The spikes of EEG even in a still state of the rat were observed. About 8 min after the administration of the compounds of the present invention, characteristic spikes appeared and continued until 40 to 60 min after the administration. In the case of GABA which is well-known as a depressive neurotransmitter having cerebral metabolic and sedative effects, a few minutes after the administration the similar spikes of EEG appeared and continued until about 25 min after the administration.

While the spikes were appeared, we observed the behavior of the animal. As a result, a sedative state was observed. However, it was not cataleptiform akinesia but natural and physiologic sedative state which immediately became wakefulness by an outside stimulation.

As apparently shown by the results of the above pharmacological test, the compounds of the present invention showed excellent neurotropic effect even at doses of the compounds on the order of one hundredth to one tenth of the dose of GABA. Furthermore, the effect of the compounds of the present invention continued longer than GABA.

(2) Analgesic effect

Groups of 10 ddY-strain male mice weighing 24–30 g were used for measurement of analgesic effect of the peptide compounds of the present invention by modified Randall-Selitto's test (Tale pressure method). Analgesic test was performed at 5 min after intracisternal injection of the test drugs. A result was shown in Table 1.

TABLE 1

| Drug | Dose (μmole/mouse) | Pain Index |
|---|---|---|
| Control | — | 1.17 ± 0.12 |
| Compound 2 | 0.1 | 1.80 ± 0.15 |
| Compound 10 | 0.1 | 1.89 ± 0.14 |
| Compound 22 | 0.1 | 1.72 ± 0.15 |
| GABA | 0.1 | 1.65 ± 0.13 |

$$\text{Pain Index} = \frac{\text{Pain threshold (g) after the administration}}{\text{Pain threshold (g) before the administration}}$$

The compounds of the present invention have the sedative effect and show the spikes of EEG similarly to GABA. The compounds of this invention have GABA-like neurotropic effect, therefore, they are useful as drugs such as a sedative, analgesic agent, cerebral metabolic agent and the like. Furthermore, the dipeptide compounds of the present invention are also useful as starting materials or intermediate for preparing the tripeptide compounds of this invention.

What is claimed is:

1. A peptide having the formula (I):

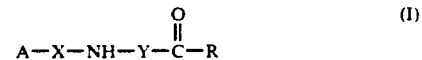

wherein A is hydrogen or an amino-protecting group; X is a member selected from the group consisting of Gly, Glu, Tyr, Asp, Phe, Ile, Ala, Pro, Leu, Hyp, Val, His, Arg, Ser, Thr, Pyr, Trp, 5-HTP, Cys, Met, τ-Glu, β-Asp; Y is a $(CH_2)_{3-6}$ or $(CH_2)_{3-6}$ having an hydroxy group; R is an hydroxy group or an oxygen atom with a carboxy-protecting group;

or a pharmaceutically acceptable salt thereof.

2. The peptide compound according to claim 1, wherein Y is a straight alkylene group of 3 carbon atoms.

3. The peptide compound according to claim 1, wherein Y is a straight alkylene group of 5 carbon atoms.

4. The peptide compound according to claim 1, wherein Y is a straight alkylene group of 3 carbon atoms having a hydroxy group.

5. The peptide compound according to claim 1, wherein X is a phenylalanine residue or a phenylalanine residue having a protecting group.

6. The peptide compound according to claim 1, wherein X is a proline residue or a proline residue having a protecting group.

7. A neurotropic agent comprising at least one peptide according to formula (I):

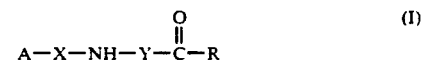

wherein A is hydrogen or an amino-protecting group; X is a member selected from the group consisting of Gly, Glu, Tyr, Asp, Phe, Ile, Ala, Pro, Leu, Hyp, Val, His, Arg, Ser, Thr, Pyr, Trp, 5-HTP, Cys, Met, τ-Glu, β-Asp; Y is a $(CH_2)_{3-6}$ or $(CH_2)_{3-6}$ having an hydroxy group; R is a hydroxy group or an oxygen atom with a carboxy-protecting group.

8. The neurotropic agent according to claim 7 which is a sedative.

9. The neurotropic agent according to claim 7 which is a cerebral metabolic agent.

10. The neurotropic agent according to claim 7 which is an analgesic agent.

* * * * *